United States Patent
Matsuhisa et al.

(10) Patent No.: US 6,734,203 B2
(45) Date of Patent: May 11, 2004

(54) FUSED IMIDAZOLIUM DERIVATIVES

(76) Inventors: Akira Matsuhisa, c/o Yamanouchi Pharmaceutical Co., Ltd., 21, Miyukigaoka, Tsukuba-shi, Ibaraki (JP), 305-8585; Isao Kinoyama, c/o Yamanouchi Pharmaceutical Co., Ltd., 21, Miyukigaoka, Tsukuba-shi, Ibaraki (JP), 305-8585; Akira Toyoshima, c/o Yamanouchi Pharmaceutical Co., Ltd., 21, Miyukigaoka, Tsukuba-shi, Ibaraki (JP), 305-8585; Takahito Nakahara, c/o Yamanouchi Pharmaceutical Co., Ltd., 21, Miyukigaoka, Tsukuba-shi, Ibaraki (JP), 305-8585; Masahiro Takeuchi, c/o Yamanouchi Pharmaceutical Co., Ltd., 21, Miyukigaoka, Tsukuba-shi, Ibaraki (JP), 305-8585; Minoru Okada, c/o Yamanouchi Pharmaceutical Co., Ltd, 21, Miyukigaoka, Tsukuba-shi, Ibaraki (JP), 305-8585

( * ) Notice: Subject to any disclaimer, the term of this patent is extended or adjusted under 35 U.S.C. 154(b) by 0 days.

(21) Appl. No.: 10/169,409
(22) PCT Filed: Feb. 14, 2001
(86) PCT No.: PCT/JP01/01036
§ 371 (c)(1), (2), (4) Date: Jul. 1, 2002
(87) PCT Pub. No.: WO01/60803
PCT Pub. Date: Aug. 23, 2001

(65) Prior Publication Data
US 2003/0114508 A1 Jun. 19, 2003

(30) Foreign Application Priority Data
Feb. 15, 2000 (JP) .................. 2000-036645
Aug. 30, 2000 (JP) .................. 2000-261489

(51) Int. Cl.$^7$ .................. A61K 31/4184; C07D 235/02
(52) U.S. Cl. .................. 514/393; 548/302.1; 546/273.1; 514/338; 514/255.05; 544/405
(58) Field of Search .................. 548/302.1; 514/393

(56) References Cited
U.S. PATENT DOCUMENTS
3,060,188 A * 10/1962 Marxer .................. 260/309.2
4,581,349 A * 4/1986 Wright .................. 514/81
5,506,361 A * 4/1996 Koh et al. .................. 548/253

FOREIGN PATENT DOCUMENTS
GB 887337 * 1/1962
GB 1 314 881 4/1973
JP 3-258765 11/1991
WO WO 97/30022 8/1997

OTHER PUBLICATIONS

Marxer, CA 55: 105820, 1961.*
Khim.–Farm.Zh., 32 (6), 10–11, 1998, with partial English translation.
Tai–Shun Lin, et al. "Synthesis of 2–3–Diaziridinyl–1, 4–naphthoquinone Sulfonate Derivatives as Potential Antineoplastic Agents." J. Med. Chem,1989, vol. 32, 1467–1471.
Sheng–Chu Kuo, et al. "Synthesis and Cytotoxicity of 1,2–Disubstituted Naphth [2,3–d] imidazole–4, 9–diones and Related Compounds" J. Med. Chem., 1996, vol. 39, 1447–1451.
Price Truitt, et al. "1,2–Disubstituted Naphth [2,3–d] imidazole–4,9–diones and Corresponding Quaternary Salts."J. Med. Chem., 1964, vol. 7(3), 362–364.

* cited by examiner

Primary Examiner—Laura L. Stockton
(74) Attorney, Agent, or Firm—Sughrue Mion, PLLC

(57) ABSTRACT

This invention relates to medicaments, particularly novel fused imidazolium derivatives useful for the treatment of cancers and novel synthetic intermediate compounds thereof.

The novel imidazolium derivatives fused with an aryl or heteroaryl ring, characterized in that the 1- and/or 3-position is substituted by an alkyl group etc. having a substituent selected from the group consisting of —ORa, —SRa and the like, have excellent anti-tumor activity and low toxicity and are useful as anticancer agents having wide margins of safety.

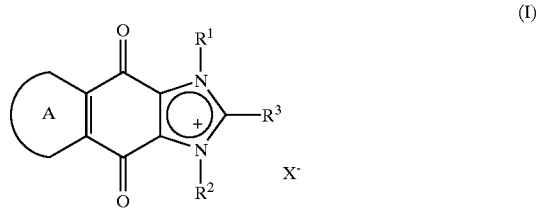

9 Claims, No Drawings

FUSED IMIDAZOLIUM DERIVATIVES

TECHNICAL FIELD

This invention relates to medicaments, particularly novel fused imidazolium derivatives useful for the treatment of cancers and novel synthetic intermediate compounds thereof.

BACKGROUND OF THE INVENTION

As imidazolium derivatives fused with aryl or heteroaryl ring and having anti-tumor activity, only the 4,9-dioxonaphtho[2,3-d]imidazolium compounds (KP-1, KP-3 and the like) of the following formula have so far been disclosed in Khim. Pharm. Zh., 32(6), 10–11 (1998).

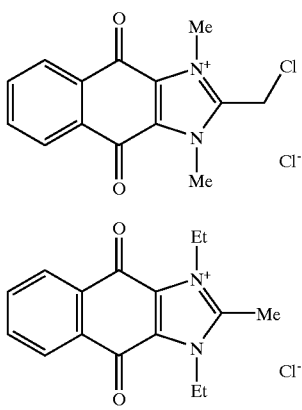

(In the formula, Et and Me respectively represent ethyl and methyl, the same shall apply hereinafter.)

J. Med. Chem., 7(3), 362–364 (1964) discloses a compound having an antimicrobial action in which $R^1$ and $R^2$ of the general formula (I) of the present invention, which will be described later, are both lower alkyl, or one is -lower alkylene-(an aryl which may have one or more substituents) and the other is —$CH_3$, —$(CH_2)_3CH_3$ or -phenyl group, or one is -lower alkylene-CO— (an aryl which may have one or more substituents) and the other is —$CH_2CH(CH_3)_2$ or —$(CH_2)_3CH_3$, but there is no disclosure on its anti-tumor activity.

Also, 4,9-dioxonaphtho[2,3-d]imidazolium derivatives in which $R^1$ and $R^2$ of the general formula (I) of the present invention are both lower alkyl groups are disclosed in J. Org. Chem. USSR, 1, 1479–85 (1965), JP-A-3-258765 and JP-A-6-59371 and the like. However, there is no disclosure on the medicinal use of these compounds.

British Patent No. 1314881 discloses 1,4-dihydro-1,4-dioxonaphthalene derivatives useful as a herbicide, and JP-B-54-25085 discloses isoquinoline-5,8-dione derivatives useful as a herbicide, respectively. Also, several 1,4-dihydro-1,4-dioxonaphthalene derivatives are commonly known by Zh. Org. Khim., 22(8), 1736–42 (1986), J. Gen. Chem. USSR, 36, 649–652 (1966) and reagent catalogs [Sigma Aldrich Library of Rare Chemicals Structure Index, with update (Aldrich Chemical Company, Inc.) and the like]. However, all of these documents do not disclose on the medicinal use of these compounds.

Imidazole derivatives fused with aryl ring are disclosed in WO 97/30022, J. Med. Chem., 39(7), 1447–1451 (1996) and J. Med. Chem., 7(3), 362–364 (1964).

DISCLOSURE OF THE INVENTION

Creation of an anticancer agent which exhibits excellent anti-tumor activity and also has low toxicity is still in great demand.

The present inventors have conducted intensive studies on anticancer agents having less side effects and found as a result of the efforts that novel imidazolium derivatives fused with an aryl or heteroaryl ring, characterized by being substituted at the 1- and/or 3-position with substituted alkyl group etc., exhibit excellent anti-tumor activity and low toxicity, thus they can be useful as anticancer agents having wide margins of safety. In addition, by finding a 2-acylamino-3-amino-1,4-quinone derivative and a fused imidazole derivative useful as their synthetic intermediates and further finding that this synthetic intermediate 2-acylamino-3-amino-1,4-quinone derivative itself also shows low toxicity and excellent anti-tumor activity, the invention has been accomplished.

That is, the invention relates to a fused imidazolium derivative represented by the following general formula (I) and a pharmaceutical composition, particularly an anticancer agent, which comprises this fused imidazolium derivative and a pharmaceutically acceptable carrier.

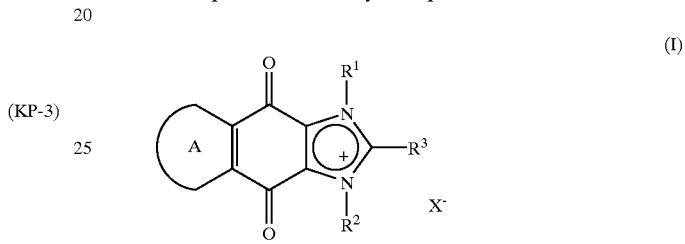

(Symbols in the formula have the following meanings;

$R^1$ and $R^2$: the same or different from each other and each represents -(lower alkyl having one or more substituents selected from group B), -(lower alkenyl having one or more substituents selected from group B), -(lower alkynyl having one or more substituents selected from group B), -RinD, -lower alkyl, -lower alkenyl or -lower alkynyl, with the proviso that at least one of $R^1$ and $R^2$ is -(lower alkyl having one or more substituents selected from group B), -(lower alkenyl having one or more substituents selected from group B), -(lower alkynyl having one or more substituents selected from group B), -(cycloalkyl having one or more substituents) or -(five- to seven-membered saturated heterocyclic ring which may have one or more substituents), group B: —$OR^a$, —$SR^a$, -prodrug-formed OH, —O-lower alkylene-$OR^a$, —O-lower alkylene —O-lower alkylene-$OR^a$, —O-lower alkylene-$NR^aR^b$, —O-lower alkylene-O-lower alkylene-$NR^aR^b$, —O-lower alkylene-$NR^c$-lower alkylene-$NR^aR^b$, —OCO—$NR^aR^b$, —$SOR^a$, —$SO_2R^a$, —$SO_2NR^aR^b$, —$NR^a$—$SO_2R^b$, —$NR^aR^b$, —$NR^c$-lower alkylene-$NR^aR^b$, —N(-lower alkylene-$NR^aR^b$)$_2$, -RinD, —$NO_2$, —CN, -halogen, —$CO_2R^a$, —$COO^-$, —$CONR^aR^b$, —$CONR^a$—O—$R^b$, —$NR^a$—$COR^b$, —$NR^a$—CO—$NR^bR^c$, —$OCOR^a$ and —CO—$R^a$, $R^a$, $R^b$ and $R^c$: the same or different from one another and each represents —H, -lower alkyl, -lower alkylene-RinD or -RinD, RinD: -(five- to seven-membered saturated heterocyclic ring which may have one or more substituents), -(cycloalkyl which may have one or more substituents), -(cycloalkenyl which may have one or more substituents), -(aryl which may have one or more substituents) or -(heteroaryl which may have one or more substituents), R³: —H or -(lower alkyl which may have one or more substituents), or R² and R³ may together form a lower alkylene having from 2 to 5 carbon atoms which may be interrupted with O, S or NR⁴ (R⁴: —H or -lower alkyl), ring A: aryl ring which may have one or more substituents or heteroaryl ring which may have one or more substituents, and X⁻: counter anion, with the proviso that X⁻ does not exist when the substituent —COO⁻ of the group B forms intramolecular salt with imidazolium cation, with the proviso that compounds having the following combinations of R¹ and R² are excluded:
(1) one is -lower alkylene-(aryl which may have one or more substituents) and the other is —CH₃, —(CH₂)₃CH₃ or -phenyl,
(2) one is -lower alkylene-CO-(aryl which may have one or more substituents) and the other is —CH₂CH(CH₃)₂ or —(CH₂)₃CH₃, or
(3) R¹ and R² are both -benzyl, —(CH₂)₂OC₂H₅ or —(CH₂)₂O—COCH₃; the same shall apply hereinafter.)

Also, the invention relates to a 2-acylamino-3-amino-1,4-quinone derivative represented by the following general formula (II) or a salt thereof, which is a synthetic intermediate of the above general formula (I) and has excellent anti-tumor activity by itself too, and to a pharmaceutical composition, particularly an anticancer agent, which contains this compound or a salt thereof and a pharmaceutically acceptable carrier.

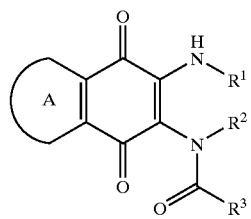

(II)

(Symbols in the formula have the following meanings;
R¹ and R²: the same or different from each other and each represents -(lower alkyl having one or more substituents selected from group B), -(lower alkenyl having one or more substituents selected from group B), -(lower alkynyl having one or more substituents selected from group B), -RinD, -lower alkyl, -lower alkenyl or -lower alkynyl, with the proviso that at least one of R¹ and R² is -(lower alkyl having one or more substituents selected from group B), -(lower alkenyl having one or more substituents selected from group B), -(lower alkynyl having one or more substituents selected from group B), -(cycloalkyl having one or more substituents) or -(five- to seven-membered saturated heterocyclic ring which may have one or more substituents), group B: —ORᵃ, —SRᵃ, -prodrug-formed OH, —O-lower alkylene-ORᵃ, —O-lower alkylene-O-lower alkylene-ORᵃ, —O-lower alkylene-NRᵃRᵇ, —O-lower alkylene-O-lower alkylene-NRᵃRᵇ, —O-lower alkylene-NRᶜ-lower alkylene-NRᵃRᵇ, —OCO—NRᵃRᵇ, —SORᵃ, —SO₂Rᵃ, —SO₂NRᵃRᵇ, —NRᵃ—SO₂Rᵇ, —NRᵃRᵇ, —NRᶜ-lower alkylene-NRᵃRᵇ, —N(-lower alkylene-NRᵃRᵇ)₂, -RinD, —NO₂, —CN, -halogen, —CO₂Rᵃ, —CONRᵃRᵇ, —CONRᵃRᵇ, —CONRᵃ—O—Rᵇ, —NRᵃ—CORᵇ, —NRᵃ—CO—NRᵇRᶜ, —OCORᵃ and —CO—Rᵃ, Rᵃ, Rᵇ and Rᶜ: the same or different from one another and each represents —H, -lower alkyl, -lower alkylene-RinD or -RinD, RinD: -(five- to seven-membered saturated heterocyclic ring which may have one or more substituents), -(cycloalkyl which may have one or more substituents), -(cycloalkenyl which may have one or more substituents), -(aryl which may have one or more substituents) or -(heteroaryl which may have one or more substituents), R³: —H or -(lower alkyl which may have one or more substituents), or R² and R³ may together form a lower alkylene having from 2 to 5 carbon atoms which may be interrupted with O, S or NR⁴ (R⁴: —H or -lower alkyl), and ring A: aryl ring which may have one or more substituents or heteroaryl ring which may have one or more substituents, with the proviso that compounds of the following table are excluded;

TABLE 2

(II-E)

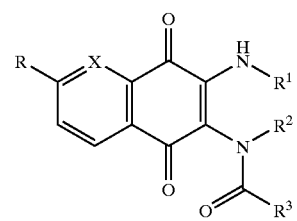

| Comp | X | R | —R¹ | —R² | —R³ |
|------|----|---|-----|-----|-----|
| E-1 | CH | H | —Me | —CH₂-(3,4-Cl—Ph) | —Me |
| E-2 | CH | H | —CH(Me)₂ | —CH₂-(3,4-Cl—Ph) | —Me |
| E-3 | CH | H | —CH₂—Ph | -(4-MeO—Ph) | —Me |
| E-4 | CH | H | —CH₂—Ph | -(3-Br—Ph) | —Me |
| E-5 | CH | H | —CH₂—Ph | —CH₂-(4-F—Ph) | —Me |
| E-6 | CH | H | —(CH₂)₂—Ph | —CH₂-(4-F—Ph) | —Me |
| E-7 | CH | H | —(CH₂)₂—OH | —Me | —Me |

TABLE 2-continued

(II-E)

| Comp | X | R | —R¹ | —R² | —R³ |
|---|---|---|---|---|---|
| E-8 | CH | H | —(CH$_2$)$_2$—OH | —CH$_2$—Ph | —Me |
| E-9 | CH | H | —(CH$_2$)$_2$—OH | -(4-MeO—Ph) | —Me |
| E-10 | CH | H | —(CH$_2$)$_2$—OH | -(4-MeO—Ph) | —Me |
| E-11 | CH | H | —(CH$_2$)$_2$—OH | -(3-Br—Ph) | —Me |
| E-12 | CH | H | —(CH$_2$)$_2$—Cl | —CH$_2$CO$_2$Et | —Me |
| E-13 | CH | H | —CH(Me)—CO$_2$H | —Me | —Me |
| E-14 | CH | H | —CH(Me)—CONHMe | —Me | —Me |
| E-15 | CH | H | —CH(Me)—CONHMe | —CH(Me)$_2$ | —Me |
| E-16 | CH | H | —CH(Me)—CONHMe | 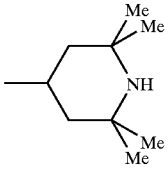 | —Me |
| E-17 | CH | H | —CH(Me)—CONHMe | —Me | —(CH$_2$)$_2$Me |
| E-18 | CH | H | —CH(Me)—CONHMe | —Me | —CH(Me)$_2$ |
| E-19 | CH | H | —CH(Me)—CONHOMe | —Me | —Me |
| E-20 | N | H | —CH(Me)—CONHMe | —Me | —Me |
| E-21 | N | Me | —CH(Me)—CONHMe | —Me | —Me |
| E-22 | CH | H | 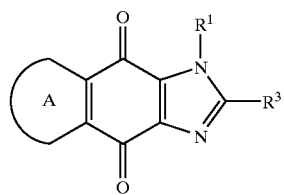 | —Me | —Me |

(in this table, Comp means compound number, Me means methyl group, Et means ethyl group and Ph means phenyl group, and in the case of a substituted phenyl group, the substituent is shown before Ph together with the substituting position, e.g., 3,4-Cl—Ph represents 3,4-dichlorophenyl, the same shall apply hereinafter).

The compounds shown in Table 2 are commonly known by British Patent No. 1314881 and JP-B-54-25085 in relation to herbicides, Zh. Org. Khim., 22(8), 1736–42 (1986) and J. Gen. Chem. USSR, 36, 649–652 (1966) in relation to their synthesis methods, and by reagent catalogs [Sigma Aldrich Library of Rare Chemicals Structure Index, with update (Aldrich Chemical Company, Inc.) and the like].)

In addition, the invention relates to a fused imidazole derivative represented by the following general formula (III) or a salt thereof, which is a novel synthetic intermediate of the aforementioned general formula (I).

(III)

(Symbols in the formula have the following meanings;
R¹: -(lower alkyl having one or more substituents selected from group B), -(lower alkenyl having one or more substituents selected from group B), -(lower alkynyl having one or more substituents selected from group B) or -(cycloalkyl having one or more substituents), with the proviso that a lower alkyl group having one or more substituents selected from the group consisting of —NH$_2$, —NMe$_2$, —NEt$_2$, —OH, -halogen and -(phenyl which may be substituted by —Cl, —F, —Me or —OMe) is excluded, group B: —OR$^a$, —SR$^a$, -prodrug-formed OH, —O-lower alkylene-OR$^a$, —O-lower alkylene-O-lower alkylene-OR$^a$, —O-lower alkylene-NR$^a$R$^b$, —O-lower alkylene-O-lower alkylene-NR$^a$R$^b$, —O-lower alkylene-NR$^c$-lower alkylene-NR$^a$R$^b$, —OCO—NR$^a$R$^b$, —SOR$^a$, —SO$_2$R$^a$, —SO$_2$NR$^a$R$^b$, —NR$^a$—SO$_2$R$^b$, —NR$^a$R$^b$, —NR$^c$-lower alkylene-NR$^a$R$^b$, —N(-lower alkylene-NR$^a$R$^b$)$_2$, -RinD, —NO$_2$, —CN, -halogen, —CO$_2$R$^a$, —CONR$^a$R$^b$, —CONR$^a$—O—R$^b$, —NR$^a$—COR$^b$, —NR$^a$—CO—NR$^b$R$^c$, —OCOR$^a$ and —CO—R$^a$, R$^a$, R$^b$ and R$^c$: the same or different from one another and each represents —H, -lower alkyl, -lower alkylene-RinD or -RinD, RinD: -(five- to seven-membered saturated heterocyclic ring which may have one or more substituents), -(cycloalkyl which may have one or more substituents), -(cycloalkenyl which may have one or more substituents), -(aryl which may have one or more substituents) or -(heteroaryl which may have one or more substituents), R³: —H or -(lower alkyl which may have one or more substituents), and ring A: aryl ring which may have one or more substituents or heteroaryl ring which may have one or more substituents, the same shall apply hereinafter.)

The compounds of general formula (I), (II) and (III) are further described.

According to this description, the term "lower" means a straight or branched form of hydrocarbon chain having from 1 to 6 carbon atoms. As the "lower alkyl", it is preferably an alkyl group having from 1 to 4 carbon atoms, and its particularly preferred examples include methyl, ethyl, n-propyl, isopropyl, n-butyl and isobutyl groups. As the "lower alkenyl", its preferred examples include vinyl, allyl, 1-propenyl, isopropenyl, 1-butenyl, 2-butenyl and 3-butenyl groups. As the "lower alkynyl", its preferred examples include ethynyl, 1-propynyl, 2-propynyl, 1-butynyl, 2-butynyl, 3-butynyl and 1-methyl-2-propynyl groups. Also, as the "lower alkylene", its preferred examples include methylene, ethylene, trimethylene and 2,2-dimethyltrimethylene groups.

The "aryl" means an aromatic hydrocarbon ring group, and its preferred examples include aryl groups having from 6 to 14 carbon atoms, more preferably phenyl, naphthyl and fluorenyl groups. Also, as the "aryl ring" in the ring A, it is a ring which forms the above aryl ring, and its preferred examples include benzene and naphthalene rings.

Examples of the "heteroaryl" include five- or six-membered monocyclic heteroaryl groups containing from 1 to 4 hetero atoms selected from N, S and O and bicyclic heteroaryl groups in which they are fused with a benzene ring or five- or six-membered monocyclic heteroaryl ring, which may be partially saturated. Also, when it contains N atom, it may form N-oxide. In this case, furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyrimidinyl, pyridazinyl, pyrazinyl and triazinyl groups are preferred as the five- or six-membered monocyclic heteroaryl, and benzofuranyl, benzothienyl, benzothiadiazolyl, benzothiazolyl, benzoxazolyl, benzoxadiazolyl, benzoimidazolyl, indolyl, isoindolyl, indazolyl, quinolyl, isoquinolyl, cinnolinyl, quinazolinyl, quinoxalinyl, benzodioxolyl, indolizinyl and imidazopyridyl groups are preferred as the bicyclic heteroaryl. As the partially saturated heteroaryl, 1,2,3,4-tetrahydroquinolyl group and the like can be exemplified. Further preferred are furyl, thienyl, imidazolyl, pyridyl, pyrazinyl, pyrimidinyl, pyridadinyl, indolyl, benzoimidazolyl, benzodioxonyl and quinolyl groups, and particularly preferred are pyridyl, pyrazinyl and pyrimidinyl groups.

The heteroaryl ring of the ring A is a ring which forms the above heteroaryl group, preferably a five- or six-membered monocyclic heteroaryl ring, and more preferred are thiophene, furan, pyrrole, imidazole, oxazole, thiazole, pyridine, pyrazine and pyrimidine rings.

As the "cycloalkyl", preferred are cycloalkyl groups having from 3 to 10 carbon atoms and particularly preferred are cyclopropyl, cyclopentyl, cyclohexyl and adamantyl groups. As the "cycloalkenyl", preferred are cycloalkenyl groups having from 3 to 8 carbon atoms and particularly preferred are cyclopentenyl and cyclohexenyl groups.

As the "counter anion", there is no particular limitation with the proviso that it is a pharmaceutically acceptable anion as a counter anion of imidazolium cation, and its preferred examples include monovalent or divalent anions such as halogen ions, organic sulfonate ions (methanesulfonate ion, ethanesulfonate ion, benzenesulfonate ion, toluenesulfonate ion and the like), acetate ion, trifluoroacetate ion, carbonate ion, sulfate ion and the like, of which halogen ions are particularly preferred.

As the "halogen", F, Cl, Br and I atoms can be exemplified, and the "halogen ion" means their ions. The "halogeno lower alkyl" is the aforementioned lower alkyl which is substituted by one or more of the halogen, and is preferably —CF₃.

The "five- to seven-membered saturated heterocyclic ring" is a five- to seven-membered monocyclic saturated heterocyclic ring containing from 1 to 4 hetero atoms selected from N, S and O, or its cross-linked ring. Preferred are tetrahydropyranyl, tetrahydrofuranyl, pyrrolidinyl, piperazinyl, azepanyl, diazepanyl, quinuclidinyl, piperidyl and morpholinyl groups.

The "-prodrug-formed OH" is a group which formed a reversible prodrug derivative that can be restored to its parent compound (original hydroxy compound) in the living body, and its examples include groups described, e.g., in *Prog. Med.*, 5: 2157–2161 (1985). Its preferred examples include —OCO-(lower alkylene which may have one or more substituents)-COOR (R represents H or lower alkyl, the same shall apply hereinafter), —OCO-(lower alkenylene which may have one or more substituents)-COOR, —OCO-(aryl which may have one or more substituents), —OCO-lower alkylene-o-lower alkylene-COOR, —OCO—CO—R, —OCO-(lower alkyl which may have one or more substituents), —OSO₂-(lower alkylene which may have one or more substituents)-COOR, —O-phthalidyl, 5-methyl-1,3-dioxolen-2-one-4-yl-methyloxy and the like.

As the substituent in the -(five- to seven-membered saturated heterocyclic ring which may have one or more substituents), -(cycloalkyl which may have one or more substituents), -(cycloalkyl which has one or more substituents), -(cycloalkenyl which may have one or more substituents), -(aryl which may have one or more substituents) or -(heteroaryl which may have one or more substituents), it is not particularly limited but is preferably from 1 to 4 substituents selected from the following group C.

Group C: -lower alkyl, -halogen, -halogeno lower alkyl, —OR$^a$, —O-lower alkylene-OR$^a$, —SR$^a$, —NR$^a$R$^b$, —NO₂, —CN, —CO₂R$^a$, —CO—NR$^a$R$^b$, —COR$^a$, —NR$^a$—COR$^b$, —SO₂NR$^a$R$^b$, -lower alkylene-NR$^a$R$^b$, -aryl, -lower alkylene-aryl and —OCO—R$^a$ (in these formulae, R$^a$ and R$^b$ are as defined in the foregoing).

Among the group C, more preferred are -lower alkyl, -halogen, -halogeno lower alkyl, —OH, —O-lower alkyl, —O-lower alkylene-OH, —O-lower alkylene-O-lower alkyl, -lower alkylene-NH₂, —NH₂, —NH-lower alkyl, —N (lower alkyl)₂, —CO₂H, —CO₂-lower alkyl, —CO—NH₂, —SO₂—NH₂, —NO₂ and —CN. The same shall apply hereinafter.

As the substituent of the "aryl ring which may have one or more substituents" or "heteroaryl ring which may have one or more substituents" in the ring A, the aforementioned groups of the group C can be cited as preferred examples, and more preferred groups are also the same as described above. Particularly preferred is —NO₂.

Though the substituent the "lower alkyl which may have one or more substituents" of R³ is not particularly limited, it is preferably a substituent of the aforementioned group B, more preferably -halogen, —OR$^a$, —SR$^a$, —NR$^a$R$^b$, —NO₂ or —CN.

In this connection, as the groups shown using R$^a$, R$^b$ and R$^c$ in the aforementioned group B and group C, groups in which R$^a$, R$^b$ and R$^c$ are —H or -lower alkyl are more desirable.

In general formula (I), the term "$R^2$ and $R^3$ together form a lower alkylene having from 2 to 5 carbon atoms which may be interrupted with O, S or $NR^4$ ($R^4$: —H or -lower alkyl)" means that $R^2$ and $R^3$ together form a lower alkylene chain which may be interrupted with O, S or $NR^4$ (preferably —$(CH_2)_4$—, —$(CH_2)_2OCH_2$— or —$(CH_2)_2N(Me)CH_2$—), and combined with the adjacent N and C atoms to form a four- to seven-membered hetero ring which is fused with imidazole ring.

Preferred compound of the compound (I) or (II) of the invention is, (1) a compound in which at least one of $R^1$ and $R^2$ is -(lower alkyl having one or more substituents selected from the group B), -(lower alkenyl having one or more substituents selected from the group B), -(lower alkynyl having one or more substituents selected from the group B), -(cycloalkyl having one or more substituents selected from the group C) or -(five- to seven-membered saturated heterocyclic ring which may have one or more substituents selected from the group C); RinD is -(five- to seven-membered saturated heterocyclic ring which may have one or more substituents selected from the group C), -(cycloalkyl which may have one or more substituents selected from the group C), -(cycloalkenyl which may have one or more substituents selected from the group C), -(aryl which may have one or more substituents selected from the group C) or -(heteroaryl which may have one or more substituents selected from the group C); $R^3$ is —H or -(lower alkyl which may have one or more substituents selected from the group B), or $R^2$ and $R^3$ may together form a lower alkylene having from 2 to 5 carbon atoms which may be interrupted with O, S or $NR^4$ ($R^4$: —H or -lower alkyl); and ring A is aryl ring which may have one or more substituents selected from the group C or heteroaryl ring which may have one or more substituents selected from the group C, (2) a compound in which at least one of $R^1$ and $R^2$ is a lower alkyl having one or more substituents selected from the group B, (3) a compound in which both of $R^1$ and $R^2$ are the same or different lower alkyl having one or more substituents selected from the group B, (4) a compound in which at least one of $R^1$ and $R^2$ is a lower alkyl having one or more substituents selected from the group consisting of —$OR^a$, —$NR^aR^b$, —$NR^a$—$COR^b$, —O-lower alkylene-$OR^a$, —O-lower alkylene-O-lower alkylene-$OR^a$, —$SR^a$, —$CONR^aR^b$, —CN, -(cycloalkyl which may have one or more substituents selected from the group C), -(five- to seven-membered saturated heterocyclic ring which may have one or more substituents selected from the group C), -(aryl which may have one or more substituents selected from the group C) and -(heteroaryl which may have one or more substituents selected from the group C), (5) a compound in which at least one of $R^1$ and $R^2$ is a lower alkyl having one or more substituents selected from the group consisting of —$OR^a$, —O-lower alkylene-$OR^a$, —O-lower alkylene-O-lower alkylene-$OR^a$, -(five- to seven-membered saturated heterocyclic ring which may have one or more substituents selected from the group C), -(aryl which may have one or more substituents selected from the group C) and -(heteroaryl which may have one or more substituents selected from the group C), (6) a compound in which at least one of $R^1$ and $R^2$ is a lower alkyl substituted by a heteroaryl group selected from furyl, thienyl, imidazolyl, pyridyl, pyrazinyl, pyrimidinyl, pyridazinyl, indolyl, benzoimidazolyl, benzodioxonyl and quinolyl group, which may have one or more substituents selected from the group C, (7) a compound in which one of $R^1$ and $R^2$ is a lower alkyl substituted by —O-lower alkyl and the other is a lower alkyl substituted by one substituent selected from the group consisting of —O-lower alkylene-O-lower alkyl, —O-lower alkylene-O-lower alkylene-O-lower alkyl, -(aryl which may have one or more substituents selected from the group C), -(heteroaryl which may have one or more substituents selected from the group C) and —O-lower alkyl, (8) a compound in which at least one of $R^1$ and $R^2$ is a lower alkyl having one substituent selected from the group consisting of -(heteroaryl selected from pyridyl, pyrazinyl and pyrimidinyl, which may have one or more substituents selected from the group C), —O-lower alkylene-O-lower alkyl and —O-lower alkyl, (9) a compound in which $R^3$ is methyl group,

(10) a compound in which the ring A is benzene ring which may have one or more substituents selected from the group C or a heteroaryl ring selected from thiophene, furan, pyrrole, imidazole, oxazole, thiazole, pyridine, pyrazine, pyridazine and pyrimidine ring, which may have one or more substituents selected from the group C,

(11) a compound in which the ring A is benzene ring which may be substituted by —$NO_2$, or

(12) a compound in which $X^-$ is a halogen ion.

Also, another preferred compound of the compound (I) of the invention is a fused imidazolium derivative in which $R^1$ and $R^2$ are the same or different from each other and each represents -(lower alkyl having one or more substituents selected from group B'), -(lower alkenyl having one or more substituents selected from group B'), -(lower alkynyl having one or more substituents selected from group B'), -(cycloalkyl which may have one or more substituents selected from group C'), -(five- or six-membered monocyclic heteroaryl which may have one or more substituents selected from group C'), -(aryl which may have one or more substituents selected from group C'), -(five- to seven-membered saturated heterocyclic ring which may have one or more substituents selected from group C'), -lower alkylene-(aryl which may have one or more substituents selected from group C'), -lower alkylene-CO-(aryl which may have one or more substituents selected from group C'), -lower alkyl, -lower alkenyl or -lower alkynyl, with the proviso that at least one of $R^1$ and $R^2$ is -(lower alkyl having one or more substituents selected from group B'). -(lower alkenyl having one or more substituents selected from group B') or -(lower alkynyl having one or more substituents selected from group B'); group B'is —$OR^a$, —$SR^a$, -prodrug-formed OH, —O-lower alkylene-RinD, —$SOR^a$, —$SO_2R^a$, —$SO_2NR^aR^b$, —$NR^a$—$SO_2R^b$, —$NR^aR^b$, —$NR^c$-lower alkylene-RinD, —N(-lower alkylene-RinD)$_2$, —$NR^c$-lower alkylene-$NR^aR^b$, —N(lower alkylene-$NR^aR^b)_2$, -(five- to seven-membered saturated heterocyclic ring which may have one or more substituents selected from group C'), -(five- or six-membered monocyclic heteroaryl which may have one or more substituents selected from group C'), -cycloalkyl, —S-lower alkylene-RinD, —$NO_2$, —CN, —$CO_2R^a$, —$CONR^aR^b$, —$NR^a$—$COR^b$, —$OCOR^a$, —CO-lower alkyl and —CO-(five- or six-membered monocyclic heteroaryl which may have one or more substituents selected from group C'); $R^a$, $R^b$ and $R^c$ are the same or different from one another and each represents —H, -lower alkyl or -RinD; RinD is -(five- to seven-membered saturated heterocyclic ring which may have one or more substituents selected from group C'), -(aryl which may have one or more substituents selected from group C') or -(five- or 6-membered monocyclic heteroaryl which may have one or more substituents selected from group C');

group C' is -lower alkyl, -halogen, —OR$^a$, —SR$^a$, —NR$^a$R$^b$, —NO$_2$, —CN, —CO$_2$R$^a$, —CO—NR$^a$R$^b$, —COR$^a$, —NR$^a$—COR$^b$, and —OCO—R$^a$; R$^3$ is —H or -lower alkyl; ring A is benzene ring which may have a substituent selected from the group consisting of -lower alkyl, —OR$^a$, —NR$^a$R$^b$, —CN, -halogen and —NO$_2$; and X$^-$ is counter anion.

Among compounds (I) of the invention, particularly preferred compounds are 1-[(6-chloro-3-pyridyl)methyl]-3-(2-methoxyethyl)-2-methyl-4,9-dioxo-4,9-dihydro-1H-naphtho[2,3-d]imidazol-3-ium, 1,2-dimethyl-4,9-dioxo-3-[(2-tetrahydrofuranyl)methyl]-4,9-dihydro-1H-naphtho[2,3-d]imidazol-3-ium, 1,3-bis(2-methoxyethyl)-2-methyl-4,9-dioxo-4,9-dihydro-1H-naphtho[2,3-d]imidazol-3-ium, 3-(2-methoxyethyl)-2-methyl-4,9-dioxo-1-(2-pyrazinylmethyl)-4,9-dihydro-1H-naphtho[2,3-d]imidazol-3-ium, 1-[3-(1H-4-imidazolyl)propyl]-3-(2-methoxyethyl)-2-methyl-4,9-dioxo-4,9-dihydro-1H-naphtho[2,3-d]imidazol-3-ium, 3-(2-methoxyethyl)-2-methyl-1-[(5-methyl-2-pyrazinyl)methyl]-4,9-dioxo-4,9-dihydro-1H-naphtho[2,3-d]imidazol-3-ium, 2-methyl-4,9-dioxo-1,3-bis(2-pyrazinylmethyl)-4,9-dihydro-1H-naphtho[2,3-d]imidazol-3-ium, 1-[2-(2-methoxyethoxy)ethyl]-3-(2-methoxyethyl)-2-methyl-4,9-dioxo-4,9-dihydro-1H-naphtho[2,3-d]imidazol-3-ium, 1-{2-[2-(2-methoxyethoxy)ethoxy]ethyl}-3-(2-methoxyethyl)-2-methyl-4,9-dioxo-4,19-dihydro-1H-naphtho[2,3-d]imidazol-3-ium, 1-(2-methoxyethyl)-2-methyl-4,9-dioxo-3-(3-pyridylmethyl)-4,9-dihydro-1H-naphtho[2,3-d]imidazol-3-ium, 3-(2-methoxyethyl)-2-methyl-4,9-dioxo-1-(2-pyridylmethyl)-4,9-dihydro-1H-naphtho[2,3-d]imidazol-3-ium, 3-(2-methoxyethyl)-2-methyl-4,9-dioxo-1-(4-pyridylmethyl)-4,9-dihydro-1H-naphtho[2,3-d]imidazol-3-ium, 1-[(2-chloro-3-pyridyl)methyl]-3-(2-methoxyethyl)-2-methyl-4,9-dioxo-4,9-dihydro-1H-naphtho[2,3-d]imidazol-3-ium, 1-[(2-hydroxy-4-pyridyl)methyl]-3-(2-methoxyethyl)-2-methyl-4,9-dioxo-4,9-dihydro-1H-naphtho[2,3-d]imidazol-3-ium, 3-(2-methoxyethyl)-1-[(6-methoxy-3-pyridyl)methyl]-2-methyl-4,9-dioxo-4,9-dihydro-1H-naphtho[2,3-d]imidazol-3-ium, 1-[(2-chloro-4-pyridyl)methyl]-3-(2-methoxyethyl)-2-methyl-4,9-dioxo-4,9-dihydro-1H-naphtho[2,3-d]imidazol-3-ium, 1-(4-chlorobenzyl)-3-(2-methoxyethyl)-2-methyl-4,9-dioxo-4,9-dihydro-1H-naphtho[2,3-d]imidazol-3-ium, 1-(4-fluorobenzyl)-3-(2-methoxyethyl)-2-methyl-4,9-dioxo-4,9-dihydro-1H-naphtho[2,3-d]imidazol-3-ium and 1,3-bis(2-methoxyethyl)-2-methyl-5-nitro-4,9-dioxo-4,9-dihydro-1H-naphtho[2,3-d]imidazol-3-ium, or tautomers thereof and their salts with halogen ions.

The compound (I) of the invention exists in tautomer forms represented by the following formula due to delocalization of the cation, and these isomers in separated forms or mixtures thereof are included in the invention. The compound mentioned herein as 1H-imidazol-3-ium derivative includes 3H-imidazol-1-ium derivative as its tautomer and mixture of both isomers. In this connection, X$^-$ does not exist when the compound (I) has a substituent —COO$^-$ and forms intramolecular salt with the imidazolium cation.

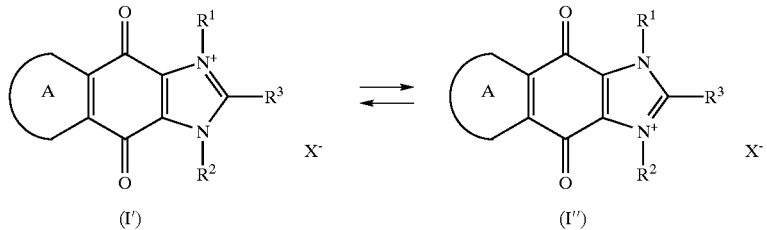

(I')        (I'')

In addition to the aforementioned salt with a counter anion, the compound (I) of the invention forms other salts in some cases depending on the kinds of substituents, and these salts are also included in the invention. In addition, the compound (II) or (III) of the invention also forms salts in some cases depending on the kinds of substituents, and these salts are also included in the invention. Though these salts are not particularly limited with the proviso that they are pharmaceutically acceptable salts, acid addition salts with an inorganic acid (hydrochloric acid, hydrobromic acid, hydroiodic acid, sulfuric acid, nitric acid, phosphoric acid and the like) and with an organic acid (formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like) can be cited as illustrative examples of acid addition salts, and salts with an inorganic base containing a metal (sodium, potassium, magnesium, calcium, aluminum and the like) or with an organic base (methylamine, ethylamine, ethanolamine, lysine, ornithine and the like) and ammonium salts and the like can be exemplified as salts with bases.

Depending on the kinds of substituents, geometrical isomers and tautomers exist in the compound (I), (II) or (III) of the invention in some cases, and these isomers in separated forms or mixture thereof are included in the invention. Also, since certain compounds of the invention have asymmetric carbon atom, isomers based on the asymmetric carbon atom can exist. The invention includes mixed and separated forms of these optical isomers. Also, compounds of the invention may sometimes form N-oxide depending on the kinds of substituents, and these N-oxide compounds are also included in the invention. In addition, various hydrates and solvates and polymorphic substances of the compound (I), (II) or (III) of the invention are also included in the invention.

Synthesis Methods

The compounds (I), (II) and (III) of the invention can be synthesized easily by using similar methods described in references, e.g., *J. Org. Chem. USSR*, 1, 1479–85 (1965), *J. Med. Chem.*, 7(3), 362–364 (1964), JP-A-3-258765, or by applying the methods known to those skilled in the art.

In this connection, depending on the kind of functional group, it may sometimes be effective from the viewpoint of synthesis techniques to replace the functional group with an appropriate protecting group, namely a group which can be easily converted into the functional group, at the stage of starting materials or synthetic intermediates. Thereafter, a desired compound can be obtained by removing the protecting group as occasion demands. Examples of such functional groups include a amino group, a hydroxyl group, a carboxyl group and the like and examples of their protecting groups include those which are described in "Protective Groups in Organic Synthesis", 2nd edition, edited by Greene and Wuts, which may be optionally used depending on the reaction conditions.

The following describes typical Synthesis methods.

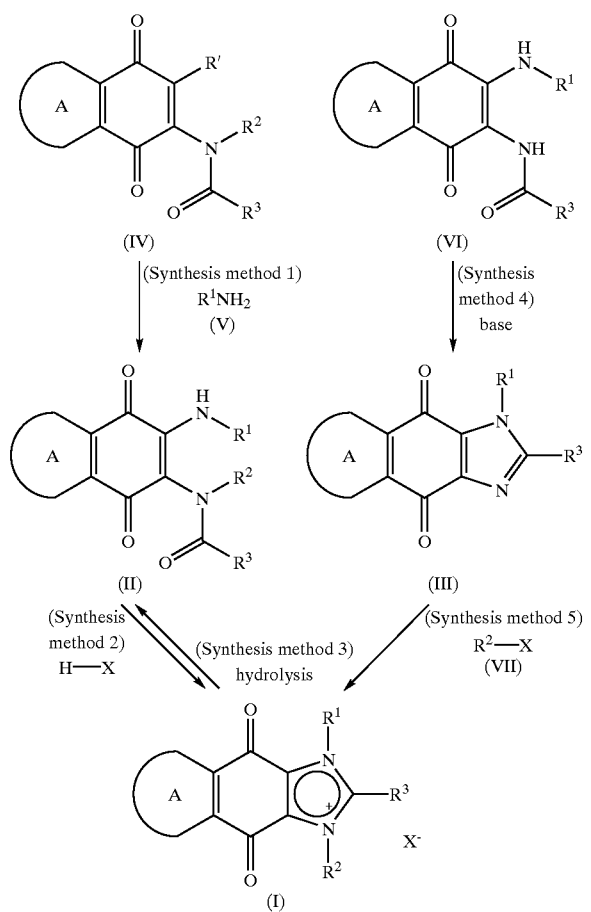

(In the formula, R' means hydrogen, methoxy or halogen group, and H—X means an acid which forms anion (preferably hydrogen fluoride, hydrogen chloride, hydrogen bromide, hydrogen iodide, methanesulfonic acid, ethanesulfonic acid and the like). The same shall apply hereinafter.)

Synthesis Method 1

The compound (II) of the invention can be synthesized in the usual procedures by allowing a compound (IV) to react with amines (V). For example, it can be synthesized by applying the methods described in *Chem. Pharm. Bull.*, 44(6), 1181–1187 (1996), *Syn. Comm.*, 27 (12), 2143–2157 (1997), *Tetrahedron. Lett.*, 39(42), 7677–7678 (1998) and the like, and it is advantageous to carry out the reaction at ambient temperature or under heating in an appropriate inert solvent (benzene and the like) using reaction equivalent amounts of the compounds (IV) and (V), or one of them in an excess amount, if necessary using an appropriate inorganic base (potassium carbonate and the like) or organic base (triethylamine and the like) as an acid capturing agent.

Synthesis Method 2

The compound (I) of the invention can be synthesized in the usual procedures by subjecting the compound (II) of the invention to cyclization and making it into a quaternary salt. For example, the reaction can be carried out by applying the method described in *J. Org. Chem. USSR*, 1, 1479–85 (1965), and it is advantageous to carry out the reaction at ambient temperature or under heating in an appropriate inert solvent (e.g., an alcohol solvent) using a reaction equivalent amount or an excess amount of an acid.

Synthesis Method 3

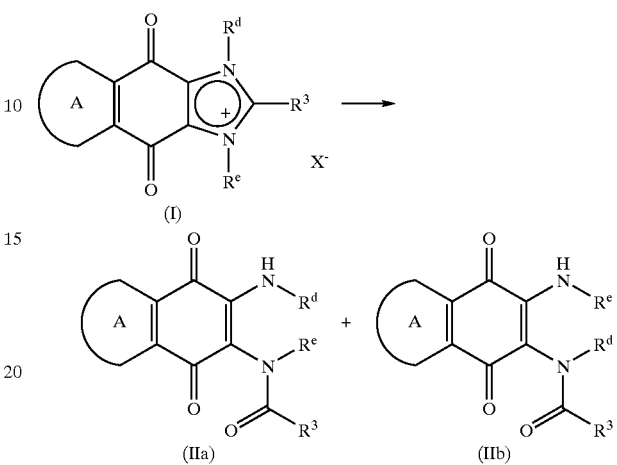

(In the formula, $R^d$ and $R^e$ are any groups defined in $R^1$ and $R^2$. The same shall apply hereinafter.)

Two compounds (IIa) and (IIb) of the invention can be synthesized by hydrolysis of the compound (I) of the invention in the usual procedures. The obtained compounds can also be made into synthetic intermediates of desired compound (I) of the invention by subjecting them to commonly known substituent-modification reactions.

The hydrolysis reaction can be carried out by applying the method described in *J. Med. Chem.*, 7(3), 362–364 (1964) and the like, and it is advantageous to carry out the reaction at ambient temperature or under heating in an appropriate inert solvent (ethanol and the like) using a reaction equivalent amount or an excess amount of a base. As the base, lithium hydroxide, sodium hydroxide, potassium hydroxide, sodium carbonate, potassium carbonate can be exemplified.

Synthesis Method 4

The compound (III) of the invention can be synthesized in accordance with the method described in *J. Med. Chem.*, 39(7), 1447–1451 (1996) and the like, by subjecting a compound (VI) to cyclization reaction in the presence of a base such as sodium hydroxide and the like.

Synthesis Method 5

The compound (I) of the invention can be synthesized by allowing the compound (III) of the invention to react with a halide (VII) to make it into a quaternary salt For example, the reaction can be carried out in accordance with the method described in *J. Med. Chem.*, 7(3), 362–364 (1964), preferably in an appropriate inert solvent using reaction equivalent amounts of the compounds (III) and (VII), or one of them in an excess amount, at ambient temperature or under heating, preferably under reflux temperature of the solvent.

In addition to the above Synthesis methods, compounds of the invention can also be synthesized by various commonly known modification methods of substituents. For example, a compound having a substituent containing sulfonyl bond can be synthesized from a compound having sulfide bond or sulfinyl bond by usual oxidation reaction. A N-oxide derivative of a compound having a N atom-containing heteroaryl group (e.g., pyridyl group) as a substituent can be synthesized by usual oxidation reaction. A compound having a carboxylic acid-containing substituent can be synthesized from a compound having ester or amide bond by usual hydrolysis reaction. A compound having an aminoalkyl group-containing substituent can be synthesized from a compound having a halogen-substituted alkyl bond by usual amination reaction. In case that the compounds (II) and (III) of the invention are in free forms, they can be made into salts by usual salt forming reaction as occasion demands.

Synthesis of Material Compounds

Some of the material compounds of the compounds of the invention are novel compounds, and these compounds can be synthesized easily in a similar manner as known material compounds or by using methods commonly known to those skilled in the art. Typical synthesis methods are shown below.

Synthesis scheme 1

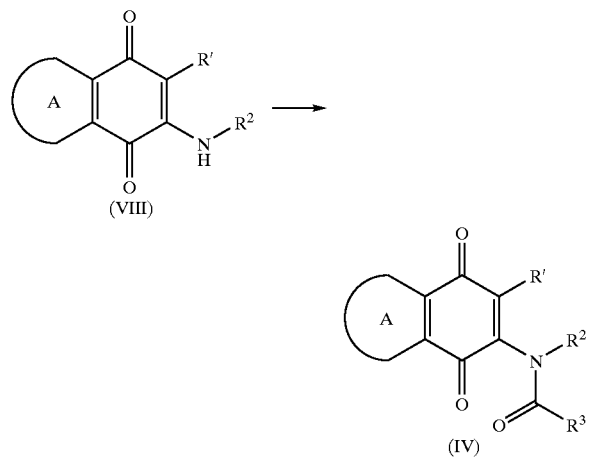

The compound (IV) can be synthesized in accordance with the method described in *J. Org. Chem. USSR*, 1, 1479–85 (1965) and the like, by a usual acylation reaction in which a compound (VIII) is allowed to react with a reactive carboxylic acid derivative such as an acid halide, acid anhydride and the like.

Synthesis scheme 2

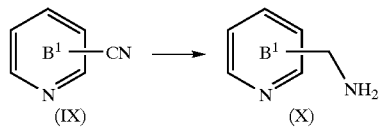

(In the formula, $B^1$ represents pyridine ring which may have one or more substituents. The same shall apply hereinafter.)

An aminomethylpyridine derivative (X) can be synthesized by the reduction of a compound (IX) in accordance with the method described in German Patent No. 3726993 (1989) and the like.

Synthesis scheme 3

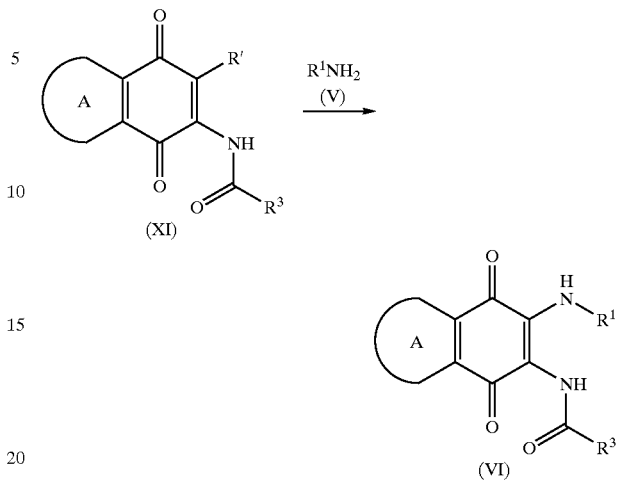

The compound (VI) can be synthesized by the amination of a compound (XI) in accordance with the method described in *J. Med. Chem.*, 39(7), 1447–1451 (1996) and the like.

Synthesis scheme 4

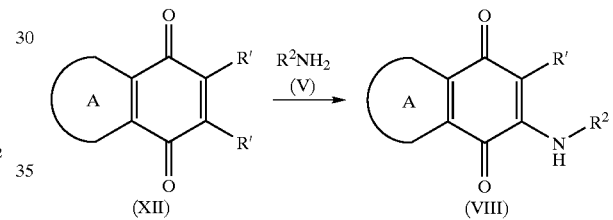

The compound (VIII) can be synthesized by the amination of a compound (XII) in accordance with the method described in *J. Het. Chem.*, 33(1), 113–117 (1996), *Syn. Comm.*, 27(12), 2143–2157 (1997), *Tetrahedron. Lett.*, 39(42), 7677–7678 (1998) and the like.

Synthesis scheme 5

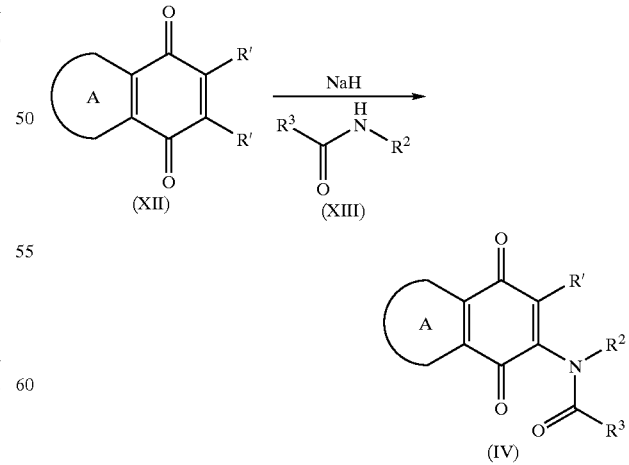

The compound (IV) can be synthesized by the amidation of the compound (XII). It is advantageous to carry out the reaction by activating a reaction equivalent amount of a compound (XIII) using an appropriate inorganic base (NaH and the like) or organic base (NaOMe and the like) in an appropriate inert solvent (N,N-dimethylformamide (DMF) and the like) and then allowing it to react with a reaction equivalent amount or an excess amount of the compound (XII) at ambient temperature or under heating.

Isolation and purification of the compounds of the invention synthesized in the above described manner are carried out by applying general chemical techniques such as extraction, concentration, evaporation, crystallization, filtration, recrystallization, various types of chromatography and the like.

Each form of isomers can be isolated by usual procedures making use of physicochemical differences among isomers. For example, racemic compounds can be converted into optically pure isomers by a conventional optical resolution method [e.g., a method in which they are made into diastereomer salts with a general optically active acid (tartaric acid and the like) and then subjected to optical resolution]. Also, a diastereomer mixture can be separated by fractional crystallization, chromatography and the like. In addition, an optically active compound can also be synthesized by using an appropriate optically active material.

Industrial Applicability

The compounds (I) and (II) of the invention are useful as anticancer agents which have excellent cancer cell growth inhibitory activity, low toxicity and wide margins of safety. Accordingly, the compounds of the invention have the inhibitory activity on growth of tumors, preferably all solid tumors and lymphomas, particularly skin cancer, bladder cancer, breast cancer, uterine cancer, ovary cancer, prostate cancer, lung cancer, colon cancer, pancreas cancer, renal cancer, gastric cancer and the like, thus they are useful for the treatment thereof. Particularly, they show excellent anti-tumor activity for many kinds of tumor types in a cancer cell growth inhibition test and an in vivo tumor growth inhibition test using a mouse tumor xenograft model, and the activity is superior to those of some existing anticancer agents. Accordingly, they are expected as therapeutic agents for tumor types which show resistance against existing anticancer agents.

Effects of the compounds of the invention were verified by the following tests.

TEST EXAMPLE 1

Cancer Cell Growth Inhibition Test (Test methods) Cell culture: Cervix cancer HeLaS3 cells or melanoma A375 cells were cultured in Dulbecco's modified Eagle's medium (DMEM) (mfd. by GIBCO) supplemented with 10% Fetal Calf Serum (FCS).

Compound evaluation: HeLaS3 cells or A375 cells were added to a gelatin-coated 96 well plate (mfd. by IWAKI) and cultured overnight in DMEM. On the next day, a dimethylsulfoxide (DMSO) solution of test compound was added thereto with varied concentrations, while fixing final concentration of DMSO solution to 0.1%. After incubation for 48 hours, cell growth was evaluated by color reaction with Alamar Blue (mfd. by Biosource).

(Results) The compounds (I) and (II) of the invention satisfactorily inhibited growth of cancer cells, and their $IC_{50}$ values were 1 μM or less.

In addition, the compounds (I) and (II) of the invention showed similarly excellent cell growth inhibitory activities also for other cancer cells (non-small cell lung cancer (EKVX, HOP-92, NCI-H358, A-549, NCI-H460), breast cancer (MDA-MB-231, MCF7), prostate cancer (PC-3), pancreas cancer (MIA PaCa-2), colon cancer (WiDr), renal cancer (A-498), gastric cancer (MKN28), bladder cancer (UC-14) and fibrosarcoma (HT-1080)).

TEST EXAMPLE 2

In vivo Tumor Growth Inhibition Test (Test methods) Melanoma A375 cells ($2\times10^6$ cells) were grafted subcutaneously into the frank of male Balb/c nude mice. When the tumor volume reached 50 to 100 $mm^3$, the test compound was intravenously administered once a day for 2 weeks. Also, saline was intravenously administered to a control group. Tumor diameter was periodically measured with a vernier caliper until the next day of the final administration. The tumor volume was calculated by the following calculation formula.

$$\text{Tumor volume } (mm^3) = \tfrac{1}{2} \times [\text{a shorter diameter } (mm)]^2 \times \text{a longer diameter } (mm)$$

(Results) In this test, the compounds (I) and (II) of the invention satisfactorily inhibited tumor growth, e.g., the compounds of Examples 4, 37, 118, 121, 148, 154, 180 and 182 showed 50% or more inhibition of tumor growth compared to the control group at a dose of 0.3 or 1 mg/kg.

The compounds of the invention showed similarly excellent anti-tumor activity also in an animal model transplanted with other cancer cells (prostate cancer (PC-3) or non-small cell lung cancer (NCI-H358, A-549 and NCI-H460)).

TEST EXAMPLE 3

Mouse Single Administration Toxicity Test (Test methods) The compounds of the invention were administered by single intravenous administration to Balb/C mice, and the presence of mortal case during the observation period of 2 weeks was evaluated.

(Results) Mortal case was not found by 3 mg/kg single administration of each of the compounds of Examples 4, 9, 35, 37, 52, 72, 121, 133, 148, 154, 158, 180, 182, 184, 185, 186, 192 and 197 of the invention. On the other hand, all of respective 2 cases died by 3 mg/kg single administration of KP-1 and KP-3 disclosed in a prior report, *Khim. Pharm. Zh.*, 32(6), 10–11 (1998). Thus, it was shown that the compounds of the invention have low toxicity in comparison with the prior reported compounds.

Accordingly, since the compounds (I) and (II) of the invention showed excellent anti-tumor activities against many kinds of tumor types with low toxicity, it was shown that they are useful as anticancer agents having good therapeutic profiles.

The pharmaceutical composition of the invention can be prepared by a generally used method using one or two or more of the compounds represented by the general formula (I) or (II) and pharmaceutically acceptable carriers (drug carriers, fillers and the like). Its administration may be either oral administration by tablets, pills, capsules, granules, powders, solutions, inhalations and the like, or parenteral administration by intravenous injection, intramuscular injection, and the like, suppositories, eye drops, ophthalmic ointments, percutaneous solutions, ointments, percutaneous adhesive preparations, transmucosal solutions, transmucosal adhesive preparations and the like.

The solid composition for use in the oral administration according to the present invention is used in the form of tablets, powders, granules and the like. In such a solid composition, one or more active substances are mixed with at least one inert filler such as lactose, mannitol, glucose, hydroxypropylcellulose, microcrystalline cellulose, starch, polyvinyl pyrrolidone, magnesium aluminate metasilicate and the like. In accordance with the usual procedures, the composition may contain inert additives such as lubricants (magnesium stearate and the like) and disintegrating agents (sodium carboxymethylstarch and the like) and solubilization assisting agent. If necessary, tablets or pills may be coated with a sugar or a gastric or enteric coating agent.

The liquid composition for oral administration includes pharmaceutically acceptable emulsions, solutions, suspensions, syrups, elixirs and the like and contains a generally used inert diluent conventionally employed, e.g., purified water or ethanol. In addition to the inert diluent, this composition may further contain an auxiliary agent such as a solubilizing agent, a moistening agent, a suspending agent and the like, as well as sweeteners, flavors, aromatics and preservatives.

The injections for parenteral administration include a sterile aqueous or non-aqueous solution, a suspension and an emulsion. Examples of the aqueous solution include distilled water for injection and saline. Examples of the non-aqueous solvent include propylene glycol, polyethylene glycol, vegetable (oils olive oil and the like), alcohols (ethanol and the like), polysorbate 80 (trade name) and the like. Such a composition may further contain a tonicity agent, a preservative, a moistening agent, an emulsifier, a dispersing agent, a stabilizer and a solubilization assisting agent. These compositions are sterilized, e.g., by filtration through a bacteria retaining filter, blending of a germicide or irradiation. Alternatively, they may be used by firstly making into sterile solid compositions and then dissolving or suspending them in sterile water or a sterile solvent for injection use prior to their use.

In the case of oral administration, suitable daily dose is usually about 0.001 to 50 mg/kg, preferably about 0.01 to 30 mg/kg, and in the case of intravenous administration, the daily dose is usually about 0.0001 to 10 mg/kg, preferably about 0.001 to 3 mg/kg, and the daily dose is divided into 1 to several doses per day. The dose may be appropriately determined for each case, depending on conditions, age, sex and the like.

BEST MODE FOR CARRYING OUT THE INVENTION

The following describes the invention further in detail based on examples. The compounds of the invention are not limited to the compounds described in the following examples. In this connection, Synthesis examples of material compounds of the compounds of the invention are shown in Reference Examples.

REFERENCE EXAMPLE 1

Saturated aqueous ammonia (17 ml) and Raney nickel (3.0 g) were added to a solution of 3-cyano-2-(dimethylamino)pyridine (2.45 g) in ethanol (50 ml) and the mixture was stirred at room temperature for 8 hours under a hydrogen atmosphere of 1 atmospheric pressure. After absorption of 760 ml of hydrogen, the catalyst was removed by filtration. By concentrating the mother liquid, 3-(aminomethyl)-2-(dimethylamino)pyridine (2.61 g) was obtained as a yellow oil.

REFERENCE EXAMPLE 2

A few drops of concentrated sulfuric acid was added to a solution of 2-chloro-3-[(2-methoxyethyl)amino]-1,4-naphthoquinone (33 g) in acetic anhydride (100 ml) and the mixture was stirred at 45° C. for 1 hour. By adding ethanol (100 ml) to the reaction solution, excess acetic anhydride was esterified. After cooling, ethyl acetate was added to the reaction solution and the mixture was washed with water and brine and then dried over anhydrous sodium sulfate. The solvent was evaporated and the residue was crystallized from diethyl ether to give N-(3-chloro-1,4-dihydro-1,4-dioxo-2-naphthalenyl)-N-(2-methoxyethyl)acetamide (29 g) as a yellow powder.

REFERENCE EXAMPLE 3

2-Methoxyethylamine (0.8 ml) was added to a solution of N-(3-chloro-1,4-dihydro-1,4-dioxo-2-naphthalenyl) acetamide (1.0 g) in benzene (20 ml) and the mixture was stirred at room temperature for 1 hour. Water was added to the reaction solution and the mixture was extracted with chloroform. The organic layer was washed with water and brine and then dried over anhydrous sodium sulfate. The solvent was evaporated and the residue was recrystallized from ethyl acetate to give N-[3-(2-methoxyethyl)amino-1, 4-dihydro-1,4-dioxo-2-naphthalenyl]acetamide (0.87 g) as a red powder.

REFERENCE EXAMPLE 4

2-(Aminomethyl)pyrazine (3.2 g) and diisopropylethylamine (5.8 ml) were added to a solution of 2,3-dichloro-1, 4-dihydro-1,4-dioxonaphthalene (3.0 g) in benzene (90 ml) and the mixture was stirred at room temperature for 8 hours. Water was added to the reaction solution and the resulting precipitate was removed by filtration and then the filtrate was extracted with ethyl acetate. The organic layer was washed with water and brine and then dried over anhydrous sodium sulfate. The solvent was evaporated and the residue was purified by silica gel column chromatography (elution with chloroform) to give 2-chloro-1,4-dihydro-1,4-dioxo-3-[(2-pyrazinylmethyl)amino]naphthalene (0.23 g) as a light brown powder.

REFERENCE EXAMPLE 5

2-Chloroacetyl chloride (3.3 ml) was added to a solution of 2-chloro-1,4-dihydro-3-methylamino-1,4-dioxonaphthalene (2.2 g) in 1,4-dioxane (30 ml) and the mixture was stirred under reflux for 14 hours. After cooling of the reaction solution, the solvent was evaporated. Ethanol was added to the residue and the resulting precipitate was collected by filtration. The obtained solid was recrystallized from ethanol to give 2-chloro-N-(3-chloro-1,4-dihydro-1,4-dioxo-2-naphthalenyl)-N-methylacetamide (2.6 g) as a yellow powder.

REFERENCE EXAMPLE 6

NaH (440 mg) was added to a solution of 2-oxopiperidine (1.0 g) in DMF (20 ml) and the mixture was stirred at room temperature for 30 minutes. This solution was added in a single portion to a solution of 2,3-dichloro-1,4-dihydro-1, 4-dioxonaphthalene (6.9 g) in DMF (150 ml) and the mixture was stirred at room temperature for 17 hours. The reaction solution was poured into saturated aqueous ammonia and the resulting precipitate was removed by filtration and then the filtrate was extracted with ethyl acetate. The organic layer was washed with water and brine and then dried over anhydrous sodium sulfate. The solvent was evaporated and the residue was purified by silica gel column chromatography (elution with ethyl acetate-hexane 1:10 solution) to give 2-chloro-1,4-dihydro-1,4-dioxo-3-(2-oxopiperidino)naphthalene (0.49 g) as a light brown powder.

REFERENCE EXAMPLE 7

2-Methoxyethylamine (1.6 ml) was added to a solution of methyl 4,7-dihydro-4,7-dioxobenzo[b]thiophene-2-carboxylate (2.4 g) in tetrahydrofuran (100 ml) and the mixture was stirred at room temperature for 27 hours. After evaporation of the solvent, the residue was purified by silica gel column chromatography (elution with chloroform) to give methyl 4,7-dihydro-5-(2-methoxyethyl)amino-4,7-dioxobenzo[b]thiophene-2-carboxylate (1.5 g) as a yellow powder.

REFERENCE EXAMPLE 8

Five drops of concentrated sulfuric acid was added to a solution of methyl 4,7-dihydro-5-(2-methoxyethyl)amino-4,7-dioxobenzo[b]thiophene-2-carboxylate (1.2 g) in acetic anhydride (20 ml) and the mixture was stirred at room temperature for 1 hour. Methanol (20 ml) was gradually added to the reaction solution and then the solvent was evaporated. Water was added to the residue and the mixture was extracted with ethyl acetate. The organic layer was washed with water and brine and then dried over anhydrous sodium sulfate. After evaporation of the solvent, the residue was purified by silica gel column chromatography (elution with ethyl acetate-hexane 1:1 solution) to give methyl 5-[N-acetyl-N-(2-methoxyethyl)amino]-4,7-dihydro-4,7-dioxobenzo[b]thiophene-2-carboxylate (0.39 g) as a reddish brown powder.

The compounds of Reference Examples 9 to 11 shown in Table 3 were obtained in a similar manner to that described in Reference Example 1, and the compound of Reference Example 12 shown in Table 4 in a similar manner to that described in Reference Example 2, the compounds of Reference Examples 13 to 15 shown in Table 4 in a similar manner to that described in Reference Example 3 and the compound of Reference Example 16 shown in Table 4 in a similar manner to that described in Reference Example 5.

EXAMPLE 1

2 M Sodium hydroxide aqueous solution (0.9 ml) was added to a solution of N-[3-(2-methoxyethyl)amino-1,4-dihydro-1,4-dioxo-2-naphthalenyl]acetamide (0.5 g) in ethanol (10 ml) and the mixture was stirred at room temperature for 15 minutes. Water was added to the reaction solution and the mixture was extracted with ethyl acetate. The organic layer was washed with water and brine and then dried over anhydrous sodium sulfate. The solvent was evaporated and the residue was collected by filtration and washed with ethanol to give 1-(2-methoxyethyl)-2-methyl-4,9-dihydro-4,9-dioxo-1H-naphtho[2,3-d]imidazole (0.58 g) as a light orange powder.

EXAMPLE 2

Benzylamine (0.5 ml) was added to a solution of N-(3-chloro-1,4-dihydro-1,4-dioxo-2-naphthalenyl)-N-(2-methoxyethyl)acetamide (0.5 g) in benzene (15 ml) and the mixture was stirred at room temperature for 4 hours. Ethyl acetate was added to the reaction solution and the mixture was washed with water and brine and then dried over anhydrous magnesium sulfate. The solvent was evaporated and the residue was crystallized from ethyl acetate-hexane to give N-(3-benzylamino-1,4-dihydro-1,4-dioxo-2-naphthalenyl)-N-(2-methoxyethyl)acetamide (0.51 g) as a red powder.

EXAMPLE 3

80% 3-chloroperbenzoic acid (0.6 g) was added to a solution of N-(2-methoxyethyl)-N-[3-(3-pyridylmethyl)amino-1,4-dihydro-1,4-dioxo-2-naphthalenyl]acetamide (0.95 g) in dichloromethane (20 ml) and the mixture was stirred at room temperature for 18 hours. Saturated sodium bicarbonate aqueous solution was added to the reaction solution and the mixture was extracted with dichloromethane. The organic layer was washed with water and brine and then dried over anhydrous sodium sulfate. The solvent was evaporated and the residue was purified by silica gel column chromatography (elution with chloroform-methanol-saturated aqueous ammonia 10:1:0.1 solution) to give 3-[({3-[N-acetyl-N-(2-methoxyethyl)]amino-1,4-dihydro-1,4-dioxo-2-naphthalenyl}amino)methyl]pyridine 1-oxide (0.84 g) as a brown amorphous solid.

EXAMPLE 4

1 M Sodium hydroxide aqueous solution (5.0 ml) was added to a solution of 1-(2-methoxyethyl)-2-methyl-3-(4-pyridylmethyl)-4,9-dihydro-4,9-dioxo-1H-naphtho[2,3-d]imidazol-3-ium chloride monohydrochloride (1.1 g) in ethanol (30 ml) and the mixture was stirred at room temperature for 30 minutes. Water was added to the reaction solution and the mixture was extracted with ethyl acetate. The organic layer was washed with water and brine and then dried over anhydrous magnesium sulfate. The solvent was evaporated and the residue was purified by silica gel column chromatography (fraction A: elution with ethyl acetate-hexane 1:1 solution, fraction B: elution with ethyl acetate). The fraction A was crystallized from diethyl ether to give N-[3-(2-methoxyethyl)amino-1,4-dihydro-1,4-dioxo-2-naphthalenyl]-N-(4-pyridylmethyl)acetamide (0.2 g) as a red powder. In this connection, the fraction B was crystallized from ethyl acetate to give a yellow powder (0.31 g) which was found to be the same compound, N-(2-methoxyethyl)-N-[3-(4-pyridylmethyl)amino-1,4-dihydro-1,4-dioxo-2-naphthalenyl]acetamide that will be described later in Example 37.

EXAMPLE 5

80% 3-chloroperbenzoic acid (0.78 g) was added to a solution of N-methyl-N-{3-[2-(methylsulfinyl)ethyl]amino-1,4-dihydro-1,4-dioxo-2-naphthalenyl}acetamide (0.52 g) in dichloromethane (10 ml) and the mixture was stirred at room temperature for 3 hours. Saturated sodium bicarbonate aqueous solution was added to the reaction solution and the mixture was extracted with dichloromethane. The organic layer was washed with water and brine and then dried over anhydrous sodium sulfate. The solvent was evaporated and the residue was purified by silica gel column chromatography (elution with chloroform-methanol 50:1 solution) to give N-methyl-N-{3-[2-(methylsulfonyl)ethyl]amino-1,4-dihydro-1,4-dioxo-2-naphthalenyl}acetamide (0.39 g) as an orange amorphous solid.

EXAMPLE 6

4 M hydrogen chloride/ethyl acetate solution (3 ml) was added to a suspension of N-[3-(2-Hydroxyethyl)amino-1,4-dihydro-1,4-dioxo-2-naphthalenyl]-N-methylacetamide (0.4 g) in ethanol (3 ml) and the mixture was stirred at 45° C. for 1 hour. After cooling, the resulting precipitate was collected by filtration and washed with ethyl acetate. The obtained solid was recrystallized from ethanol-ethyl acetate to give 1-(2-hydroxyethyl)-2,3-dimethyl-4,9-dihydro-4,9-dioxo-1H-naphtho[2,3-d]imidazol-3-ium chloride (0.28 g) as a colorless powder.

EXAMPLE 7

Benzyl bromide (1.9 ml) was added to a solution of 1-isopropyl-2-methyl-4,9-dihydro-4,9-dioxo-1H-naphtho[2,3-d]imidazole (0.8 g) in acetonitrile (20 ml) and the mixture was stirred under reflux for 6 hours. After cooling, the resulting precipitate was collected by filtration and washed with ethyl acetate. The obtained solid was recrystallized from methanol to give 1-benzyl-3-isopropyl-2-methyl-4,9-dihydro-4,9-dioxo-1H-naphtho[2,3-d]imidazol-3-ium bromide (0.47 g) as a yellow powder.

EXAMPLE 8

By the similar method of Example 6, 1-(2-hydroxy-3-pyridyl)methyl-3-(2-methoxyethyl)-2-methyl-4,19-dihydro-4,9-dioxo-1H-naphtho[2,3-d]imidazol-3-ium chloride (0.39 g) was obtained as a light brown powder from N-(2-methoxyethyl)-N-{3-[(2-methoxy-3-pyridyl)methyl]amino-1,4-dihydro-1,4-dioxo-2-naphthalenyl}acetamide (0.49 g).

EXAMPLE 9

4 M Hydrogen chloride/ethyl acetate solution (10 ml) was added to a solution of N-{3-[(6-chloro-3-pyridyl)methyl]amino-1,4-dihydro-1,4-dioxo-2-naphthalenyl}-N-(2-methoxyethyl)acetamide (0.8 g) in ethanol (10 ml) and the mixture was stirred at room temperature for 1 day. The solvent was evaporated and the residue was collected by filtration and washed with ethyl acetate to give 1-[(6-chloro-3-pyridyl)methyl]-3-(2-methoxyethyl)-2-methyl-4,9-dioxo-4,9-dihydro-1H-naphtho[2,3-d]imidazol-3-ium chloride (0.82 g) as a light yellow powder.

EXAMPLE 10

2 M Dimethylamine/tetrahydrofuran solution (3.0 ml) was added to a solution of 2-chloro-N-[1,4-dihydro-3-(2-methoxyethyl)amino-1,4-dioxo-2-naphthalenyl]-N-methylacetamide (0.5 g) in tetrahydrofuran (30 ml) and the mixture was stirred at room temperature for 18 hours. Water was added to the reaction solution and the mixture was extracted with ethyl acetate. The organic layer was washed with water and brine and then dried over anhydrous magnesium sulfate. The solvent was evaporated and the residue was crystallized from ethanol to give N-[1,4-dihydro-3-(2-methoxyethyl)amino-1,4-dioxo-2-naphthalenyl]-N-methyl-2-(dimethylamino)acetamide (0.19 g) as a brown powder.

EXAMPLE 11

2-Methoxyethylamine (0.15 ml) was added to a solution of methyl 5-[N-acetyl-N-(2-methoxyethyl)amino]-4,7-dihydro-4,7-dioxobenzo[b]thiophene-2-carboxylate (0.39 g) in tetrahydrofuran (30 ml) and the mixture was stirred at room temperature for 6.5 hours. The solvent was evaporated and the residue was purified by silica gel column chromatography (elution with hexane-ethyl acetate 50:1 solution) to give methyl 5-[N-acetyl-N-(2-methoxyethyl)amino]-4,7-dihydro-6-(2-methoxyethyl)amino-4,7-dioxobenzo[b]thiophene-2-carboxylate (0.39 g) as a reddish purple oil.

EXAMPLE 12

4 M Hydrogen chloride/ethyl acetate solution (2.5 ml) was added to a suspension of 3-{[3-(N-acetyl-N-methyl)amino-1,4-dihydro-1,4-dioxo-2-naphthalenyl]amino}propionamide (0.32 g) in methanol (30 ml) and the mixture was stirred at room temperature for 16 hours. The solvent was evaporated and the residue was stirred in ethanol with heating. After cooling, the resulting precipitate was collected by filtration and washed with ethanol to give 1-(2-carboxyethyl)-4,9-dihydro-2,3-dimethyl-4,9-dioxo-1H-naphtho[2,3-d]imidazol-3-ium chloride (0.15 g) as a colorless powder.

In a similar manner to those described in the above Examples 1 to 9, the Example compounds described in Tables 6 to 20 were obtained.

Structural formula and physicochemical properties of the reference example compounds are shown in Tables 3 to 5, and those of the Example compounds in Tables 6 to 20. In addition, the compounds having the chemical structures described in Tables 21 to 27 can be easily synthesized by almost the same methods described in the above Examples or the aforementioned processes, or by applying thereto slight modifications which are obvious to those skilled in the art.

Abbreviations in the tables respectively indicate as follows, Ref: reference example; Ex: Example; Co: compound number; Sal; salt; Sy: synthesis method (each numeral indicates the example number, showing that the compound was synthesized by the same method of this example); -: does not exist; Dat: physicochemical properties {F: FAB-MS (M)$^+$; F': FAB-MS (M)$^-$; F+: FAB-MS (M+H)$^+$; F-; FAB-MS (M-H)$^-$; E: EI-MS (M)$^+$; N1: $^1$H-NMR (DMSO-d$_6$, TMS internal standard) characteristic peaks δ ppm}; i-Pr: isopropyl; c-Pr: cyclopropyl; Ad: 1-adamantyl; Ac: acetyl; Bn: benzyl; Pipe: piperidino; Morp: morpholino; Py2: 2-pyridyl; Py3: 3-pyridyl; Py4: 4-pyridyl; Th: 2-thienyl; Fu: 2-furyl; Thf: 2-tetrahydrofuranyl; Pyr: 2-pyrazinyl; 5-MePyr: 5-methyl-2-pyrazinyl; Pym: 4-pyrimidinyl; Qu: 3-quinolyl; Dio: 4-benzodioxolyl; Im: 4-imidazolyl; Bim: 2-benzoimidazolyl; and In: 2-indolyl. In this connection, the numeral before each substituent indicates its substitution position, e.g., 3,4-Cl means that —Cl is substituted at the 3- and 4-positions respectively.

TABLE 3

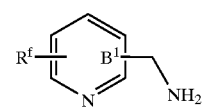

(Xa)

| Ref | B$^1$ | —R$^f$ | Dat |
|---|---|---|---|
| 1 | Py3 | 2-NMe$_2$ | F+: 152 |
| 9 | Py3 | 6-NMe$_2$ | F+: 152 |
| 10 | Py4 | 2-NMe$_2$ | F+: 152 |
| 11 | Py3 | 2-OMe | E: 138 |

TABLE 4

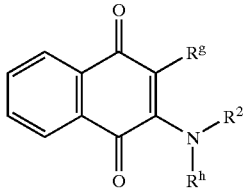

(IVa) or (VIa) or (VIIIa)

| Ref | —R$^g$ | —R$^h$ | R$^2$ | Dat |
|---|---|---|---|---|
| 2 | —Cl | —Ac | —(CH$_2$)$_2$OMe | N1: 1.88(3H, s), 2.99(3H, s), 3.3–3.9(4H, m), 7.9–8.2(4H, m) |
| 3 | —NH—(CH$_2$)$_2$OMe | —Ac | —H | F+: 289 |
| 4 | —Cl | —H | —CH$_2$Pyr | F': 299 |
| 5 | —Cl | —COCH$_2$Cl | —Me | F: 298 |
| 6 | —Cl | —CO(CH$_2$)$_4$— | | F+: 290 |
| 12 | —Cl | —Ac | —CH$_2$Pyr | F': 341 |
| 13 | —NH—CH$_2$(Py3) | —Ac | —H | F+: 322 |
| 14 | —NH—CH$_2$(Py4) | —Ac | —H | F+: 322 |
| 15 | —NH—CH$_2$(Pyr) | —Ac | —H | F+: 323 |
| 16 | —Cl | —COCH$_2$OMe | —Me | F+: 294 |

TABLE 5

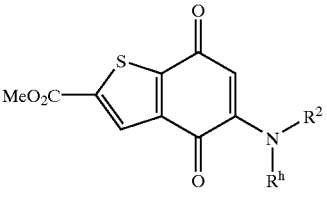

(IVb) or (VIIIb)

| Ref | R$^h$ | R$^2$ | Dat |
|---|---|---|---|
| 7 | —H | —(CH$_2$)$_2$OMe | F+: 296 |
| 8 | —Ac | —(CH$_2$)$_2$OMe | F+: 338 |

TABLE 6

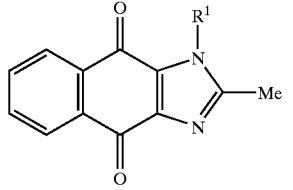

(IIIa)

| Ex. | —R$^1$ | Dat |
|---|---|---|
| 1 | —(CH$_2$)$_2$OMe | F+: 271 |
| 13 | —CH$_2$(Py3) | F+: 304 |
| 14 | —CH$_2$(Py4) | F+: 304 |
| 15 | —CH$_2$(Pyr) | F+: 305 |

TABLE 7

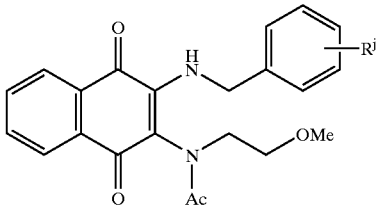

(IIc)

| Ex | —R$^j$ | Sy | Dat |
|---|---|---|---|
| 2 | —H | — | F+: 379<br>N1: 1.34(3H, br), 3.06(3H, s), 3.1–3.8(4H, m), 4.5–4.8(2H, m), 7.2–7.4(5H, m), 7.77(1H, dt), 7.85(1H, dt), 7.93(1H, br), 7.98(1H, d), 8.03(1H, d) |
| 16 | 2-Cl | 2 | F+: 413 |
| 17 | 3-Cl | 2 | F+: 413 |

TABLE 7-continued (IIc)

| Ex | —R$^i$ | Sy | Dat |
|---|---|---|---|
| 18 | 4-Cl | 2 | F+: 413 |
| | | | N1: 1.39(3H, br), 3.06(3H, s), 3.1–3.4(2H, m), 3.4–3.5(1H, m), 3.6–3.9(1H, m), 4.5–4.8(2H, m), 7.27(2H, d), 7.38(2H, d), 7.7–8.1(4H, m) |
| 19 | 3,4-Cl | 2 | F: 447 |
| 20 | 2-OMe | 2 | F+: 409 |
| 21 | 3-OMe | 2 | F+: 409 |
| 22 | 4-OMe | 2 | F+: 409 |
| 23 | 4-Ph | 2 | F+: 455 |
| 24 | 2-CN | 2 | F+: 404 |
| 25 | 3-CN | 2 | F+: 404 |
| 26 | 4-CN | 2 | F+: 404 |
| 27 | 4-SO$_2$NH$_2$ | 2 | F+: 458 |
| 28 | 4-CF$_3$ | 2 | F+: 447 |
| 29 | 4-F | 2 | F+: 397 |
| | | | N1: 1.40(3H, br), 3.06(3H, s), 3.1–3.6(3H, m), 3.79(1H, br), 4.5–4.8 (2H, m), 7.1–7.2(2H, m), 7.2–7.5(2H, m), 7.7–8.2(4H, m) |
| 30 | 4-Br | 2 | F+: 457, 459 |
| 31 | 3-CH$_2$NH$_2$ | 2 | F+: 408 |
| 32 | 4-CH$_2$NH$_2$ | 2 | F: 407 |
| 33 | 3-NO$_2$ | 2 | F+: 424 |
| 34 | 4-NO$_2$ | 2 | F+: 424 |
| | | | N1: 1.39(3H, br), 3.07(3H, s), 3.1–3.6(3H, m), 3.6–3.9(1H, m), 4.6–5.0(2H, m), 7.54(2H, d), 7.7–8.2(5H, m), 8.19(2H, d) |

TABLE 8

(IId)

| Ex | B$^1$ | —R$^f$ | Sy | Dat |
|---|---|---|---|---|
| 3 | Py3 | 1-oxide | — | F+: 396 |
| 35 | Py3 | —H | 2 | F+: 380 |
| | | | | N1: 1.40(3H, s), 3.06(3H, s), 3.1–3.8(4H, m), 4.6–4.8(2H, m), 7.34 (1H, dd), 7.6–8.1(6H, m), 8.4–8.5(2H, m) |
| 36 | Py2 | —H | 2 | F+: 380 |
| | | | | N1: 1.62(3H, s), 3.06(3H, s), 3.2–3.9(4H, m), 4.5–5.0(4H, m), 7.2–7.5(2H, m), 7.7–8.2(6H, m), 8.54(1H, d) |
| 37 | Py4 | —H | 2 | F+: 380 |
| | | | | N1: 1.38(1H, br), 3.07(3H, s), 3.1–3.8(4H, m), 4.6–4.8(2H, m), 7.26 (2H, d), 7.77(1H, dt), 7.85(1H, dt), 7.95(1H, d), 8.01(1H, d), 8.48 (2H, d) |
| 38 | Py3 | 2-Cl | 2 | F+: 414 |
| | | | | N1: 1.49(3H, s), 3.07(3H, s), 3.1–3.4(2H, m), 3.4–3.6(1H, m), 3.6–3.8(1H, m), 4.6–4.9(2H, m), 7.3–7.5(1H, m), 7.7–8.2(6H, m) |
| 39 | Py3 | 6-Cl | 2 | F+: 414 |
| | | | | N1: 1.47(3H, br), 3.07(3H, s), 3.1–3.6(3H, m), 3.6–4.0(1H, m), 4.6–4.9(2H, m), 7.48(1H, m), 7.6–8.1(6H, m), 8.34(1H, d) |
| 40 | Py3 | 2-OMe | 2 | F+: 410 |
| 41 | Py3 | 6-OMe | 2 | F+: 410 |
| | | | | N1: 1.49(3H, s), 3.07(3H, s), 3.1–3.5(3H, m), 3.6–3.9(4H, m), 4.5–4.8(2H, m), 6.79(1H, d), 7.5–7.7(1H, m), 7.7–8.2(5H, m) |

TABLE 8-continued

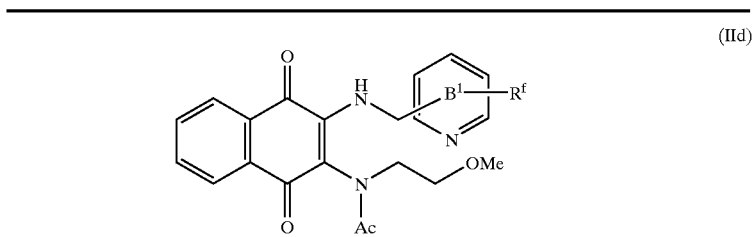

(IId)

| Ex | B¹ | —Rᶠ | Sy | Dat |
|---|---|---|---|---|
| 42 | Py3 | 2-NMe₂ | 2 | F+: 423 |
| 43 | Py3 | 6-NMe₂ | 2 | F+: 423 |
| 44 | Py3 | 5-Me | 2 | F+: 394 |
| 45 | Py3 | 6-Me | 2 | F: 393 |
| 46 | Py3 | 6-CF₃ | 2 | F+: 448 |
| 47 | Py4 | 2-Cl | 2 | F+: 414 |
| | | | | N1: 1.48(3H, br), 3.09(3H, s), 3.1–3.6(3H, m), 3.6–3.9(1H, m), 4.5–5.0(2H, m), 7.33(1H, d), 7.45(1H, s), 7.6–8.2(5H, m), 8.34(1H, d) |
| 48 | Py4 | 2-NMe₂ | 2 | F+: 423 |
| 49 | Py4 | 2-OMe | 2 | F+: 410 |

TABLE 9

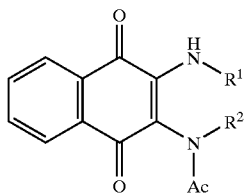

(IIe)

| Ex | —R¹ | —R² | Sy | Dat |
|---|---|---|---|---|
| 4 | —(CH₂)₂OMe | —CH₂(Py4) | — | F+: 380 |
| | | | | N1: 1.19(3H, s), 3.26(3H, s), 3.47(4H, br), 4.27(1H, d), 4.81(1H, d), 7.10(1H, br), 7.35 (2H, d), 7.74(1H, dt), 7.82(1H, dt), 7.92 (1H, d), 7.98(1H, d), 8.41(2H, d) |
| 50 | —(CH₂)₂OMe | —(CH₂)₂OMe | 2 | N1: 1.83(3H, s), 3.0–3.8(14H, m), 6.9–7.1 (1H, m), 7.7–7.9(2H, m), 7.9–8.1(2H, m) |
| 51 | —(CH₂)₂OMe | —Bn | 2 | N1: 1.88(3H, s), 3.23(3H, s), 3.3–3.5(4H, m), 4.4–4.7(2H, m), 6.91(1H, br), 7.1–7.4 (5H, m), 7.6–8.1 (4H, m) |
| 52 | —(CH₂)₂OMe | —CH₂(Py3) | 4 | F+: 380 |
| | | | | N1: 1.87(3H, s), 3.25(3H, s), 3.4–3.6(4H, m), 4.31(1H, d), 4.81(1H, d), 7.08(1H, br), 7.23(1H, dd), 7.6–7.8(2H, m), 7.81(1H, t), 7.88(1H, d), 7.98(1H, d), 8.37(1H, d), 8.45(1H, s) |
| 53 | —Bn | —Bn | 2 | F+: 411 |
| 54 | —CH₂(Py4) | —Bn | 2 | F+: 412 |
| 55 | —CH₂(Py3) | —Bn | 2 | F+: 412 |
| 56 | —(CH₂)₂Ph | —(CH₂)₂OMe | 2 | F+: 393 |
| 57 | —CH₂Th | —(CH₂)₂OMe | 2 | F+: 387 |
| 58 | —CH₂Fu | —(CH₂)₂OMe | 2 | F+: 369 |
| 59 | —CH₂Pyr | —(CH₂)₂OMe | 2 | F+: 381 |
| | | | | N1: 1.60(3H, s), 3.07(3H, s), 3.2–3.8(4H, m), 4.5–5.3(2H, m), 7.5–8.2(5H, m), 8.5–8.8(3H, m) |
| 60 | —CH₂Qu | —(CH₂)₂OMe | 2 | F+: 430 |
| 61 | —(CH₂)₂(Py2) | —(CH₂)₂OMe | 2 | F+: 394 |
| 62 | —(CH₂)₂(Py3) | —(CH₂)₂OMe | 2 | E: 393 |
| 63 | —(CH₂)₂(Py4) | —(CH₂)₂OMe | 2 | F+: 394 |
| 64 | —(CH₂)₂In | —(CH₂)₂OMe | 2 | F+: 432 |
| 65 | —CH₂Dio | —(CH₂)₂OMe | 2 | F+: 423 |
| 66 | —(CH₂)₃Im | —(CH₂)₂OMe | 2 | F+: 397 |
| 67 | —(CH₂)₂Im | —(CH₂)₂OMe | 2 | F+: 383 |
| 68 | —CH₂Bim | —(CH₂)₂OMe | 2 | F+: 419 |
| 69 | —(CH₂)₂O(CH₂)₂NH₂ | —(CH₂)₂OMe | 2 | F+: 376 |

TABLE 9-continued

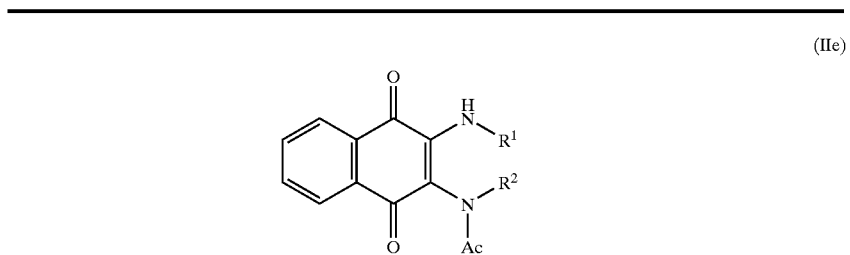

(IIe)

| Ex | —R¹ | —R² | Sy | Dat |
|----|-----|-----|-----|-----|
| 70 | —(CH₂)₅NH₂ | —(CH₂)₂OMe | 2 | F+: 374 |
| 71 | —(CH₂)₂O(CH₂)₂—O(CH₂)₂NH₂ | —(CH₂)₂OMe | 2 | F+: 420 |

TABLE 10

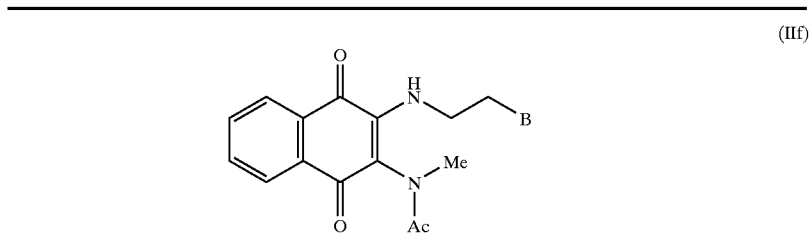

(IIf)

| Ex | —B | Sy | Dat |
|----|-----|-----|-----|
| 5 | —SO₂Me | — | F+: 351 |
| 72 | —OMe | 2 | F+: 303 |
|    |      |   | N1: 1.83(3H, s), 2.92(3H, s), 3.29(3H, s), 3.4–3.7(4H, m), 7.11(1H, br), 7.7–7.9(2H, m), 7.9–8.1(2H, m) |
| 73 | —OPh | 2 | N1: 1.83(3H, s), 2.93(3H, s), 3.6–3.9(2H, m), 4.21 (2H, t), 6.8–7.1 (3H, m), 7.2–7.5(3H, m), 7.7–7.9(2H, m), 7.9–8.1(2H, m) |
| 74 | —OBn | 2 | N1: 2.89(3H, s), 3.90(2H, t), 4.19(3H, s), 4.45(2H, s), 4.89(2H, t), 7.1–7.5(5H, m), 7.9–8.1(2H, m), 8.1–8.3(2H, m) |
| 75 | —NMe₂ | 2 | F+: 316 |
|    |       |   | N1: 1.83(3H, s), 2.18(6H, s), 2.4–2.6(2H, m), 2.94(3H, s), 3.2–3.5 (2H, m), 7.14(1H, t), 7.7–7.9(2H, m), 7.9–8.1 (2H, m) |
| 76 | —OEt | 2 | F+: 317 |
|    |      |   | N1: 1.10(3H, t), 1.82(3H, s), 2.92(3H, s), 3.3–3.7(6H, m), 7.09(1H, br), 7.7–7.9(2H, m), 7.9–8.1(2H, m) |
| 77 | —OPr | 2 | F+: 331 |
|    |      |   | N1: 0.85(3H, t), 1.4–1.6(2H, m), 1.83(3H, s), 2.92(3H, s), 3.37(2H, t), 3.4–3.7(4H, m), 7.08(1H, br), 7.7–7.9(2H, m), 7.9–8.1(2H, m) |
| 78 | —O(i-Pr) | 2 | F+: 331 |
|    |          |   | N1: 1.07(6H, d), 1.82(3H, s), 2.92(3H, s), 3.4–3.7(5H, m), 7.08(1H, br), 7.7–7.9(2H, m), 7.9–8.1(2H, m) |
| 79 | —O(CH₂)₂NH₂ | 2 | F+: 332 |
| 80 | —OCH₂(Py3) | 2 | F+: 413 |
|    |            |   | N1: 1.79(3H, s), 2.90(3H, s), 3.5–3.8(4H, m), 4.55(2H, s), 7.1–7.3 (1H, m), 7.2–7.5(1H, m), 7.7–7.9(3H, m), 7.9–8.1 (2H, m), 8.4–8.6 (2H, m) |
| 81 | —SMe | 2 | F+: 319 |
| 82 | —NEt₂ | 2 | F+: 344 |
| 83 | —N(i-Pr)₂ | 2 | F+: 372 |
| 84 | -Pipe | 2 | F+: 356 |
| 85 | -Morp | 2 | F+: 358 |
| 86 | —NHAc | 2 | F+: 330 |
|    |       |   | N1: 1.81(6H, s), 2.90(3H, s), 3.2–3.7(4H, m), 7.36(1H, br), 7.7–8.2 (5H, m) |
| 87 | —OCONHPh | 2 | F+: 408 |
| 88 | —CONH₂ | 2 | F+: 316 |
| 89 | —CN | 2 | F+: 298 |
| 90 | —O(CH₂)₂OMe | 2 | F+: 347 |

TABLE 11

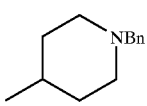

(IIe)

| Ex | —R¹ | —R² | Sy | Dat |
|---|---|---|---|---|
| 91 | —(CH₂)₃OMe | —Me | 2 | N1: 1.7–2.0(5H, m), 2.92(3H, s), 3.25(3H, s), 3.3–3.6(4H, m), 7.2–7.5(1H, m), 7.6–8.2(4H, m) |
| 92 | —(CH₂)₃NMe₂ | —Me | 2 | F+: 330 |
| 93 | —CH₂(Py2) | —Me | 2 | F+: 336<br>N1: 1.5–2.2(3H, m), 2.7–3.0(3H, m), 4.5–5.0 (2H, m), 7.2–7.5(2H, m), 7.6–8.3(6H, m), 8.4–8.7(1H, m) |
| 94 | —CH₂(Py3) | —Me | 2 | F+: 336 |
| 95 | —CH₂(Py4) | —Me | 2 | F+: 336 |
| 96 | —CH₂CF₃ | —Me | 2 | F+: 327 |
| 97 | —CH₂Thf | —Me | 2 | F+: 329 |
| 98 | —CH₂CONH₂ | —Me | 2 | F+: 302 |
| 99 | —CH₂CN | —Me | 2 | F+: 284 |
| 100 | 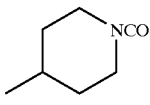 | —Me | 2 | F+: 418 |
| 101 | (4-NCO₂Et piperidinyl-methyl) | —Me | 2 | F': 399 |
| 102 | (2-MeO, 2-Me cyclohexyl) | —Me | 2 | F+: 357 |
| 103 | —CH(Me)Ph | —(CH₂)₂OMe | 2 | F+: 375 |
| 104 | —CH₂Pym | —(CH₂)₂OMe | 2 | F+: 381<br>N1: 1.61 (3H, s), 3.08(3H, s), 3.2–3.9(4H, m), 4.6–5.0(2H, m), 7.4–7.6(1H, m), 7.7–8.1(5H, m), 8.75(1H, d), 9.12(1H, d) |
| 105 | —(CH₂)₂OMe | —CH₂Pyr | 2 | F+: 381<br>N1: 1.88(3H, s), 3.26(3H, s), 3.4–3.9(4H, m), 4.3–5.3(2H, m), 7.6–8.1(5H, m), 8.3–8.6(2H, m), 8.79(1H, d) |
| 106 | —CH₂(5-MePyr) | —(CH₂)₂OMe | 2 | F+: 395<br>N1: 1.61(3H, s), 2.47(3H, s), 3.07(3H, s), 3.2–3.8(4H, m), 4.6–5.0(2H, m), 7.7–8.1(5H, m), 8.4–8.6(2H, m) |

TABLE 12

| Ex | —R¹ | —R² | Sy | Dat |
|---|---|---|---|---|
| 107 | —CH₂Pyr | —CH₂Pyr | 2 | F+: 415<br>N1: 1.72(3H,s), 4.3–5.3(4H,m), 7.6–8.1 (4H,m), 8.2–8.7(5H,m), 8.69(1H,s), 8.79 (1H,s) |
| 108 | —CH₂(Py4) | —CH₂Pyr | 2 | F+: 414<br>N1: 1.58(3H,br), 4.2–5.1(4H,m), 7.29(2H, d), 7.6–8.1(4H,m), 8.28(1H,s), 8.3–8.7(4 H,m), 8.78(1H,d) |
| 109 | —(CH₂)₁₇Me | —(CH₂)₂OMe | 2 | F+: 541 |
| 110 | —CH₂Ad | —(CH₂)₂OMe | 2 | F: 437 |
| 111 | —CH₂CHPh₂ | —(CH₂)₂OMe | 2 | F: 469 |

TABLE 12-continued
| Ex | —R¹ | —R² | Sy | Dat |
|---|---|---|---|---|
| 112 | —(CH₂)₂O(CH₂)₂OMe | —(CH₂)₂OMe | 2 | F: 391<br>N1: 1.84(3H,s), 3.0–3.9(18H,m), 6.9–7.2 (1H,m), 7.7–7.9(2H,m), 7.9–8.1 (2H,m) |
| 113 | —(CH₂)₂O(CH₂)₂O—(CH₂)₂OMe | —(CH₂)₂OMe | 2 | F: 435 |
| 114 | —(CH₂)₂O(4-BnO-Ph) | —(CH₂)₂OMe | 2 | F: 515 |
TABLE 13
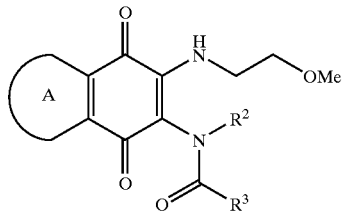
(IIg)
| Ex | A | —R² | —R³ | Sy | Dat |
|---|---|---|---|---|---|
| 10 | phenyl | —Me | —CH₂NMe₂ | — | F+: 346 |
| 11 | MeO₂C-thiophene | —(CH₂)₂OMe | —Me | — | F+: 411 |
| 115 | phenyl | —Me | —CH₂Cl | 2 | F+: 337 |
| 116 | phenyl | —Me | —CH₂OMe | 2 | F+: 333 |
| 117 | phenyl | —(CH₂)₄— | | 2 | F+: 329 |
TABLE 14
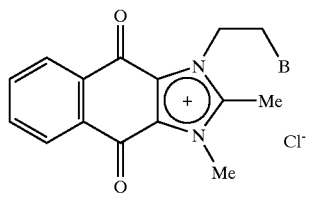
(Ia)
| Ex | —B | Sal | Sy | Dat |
|---|---|---|---|---|
| 6 | —OH | — | — | F−: 270<br>N1: 2.90(3H, s), 3.8(2H, br), 4.17(3H, s), 4,74(2H, t), 7.9–8.2(4H, m) |
| 118 | —OMe | — | 6 | F: 285<br>N1: 2.89(3H, s), 3.25(3H, s), 3.77(2H, t), 4.20(3H, s), 4.8–5.0(2H, m), 7.9–8.3(4H, m) |

TABLE 14-continued (Ia)

| Ex | —B | Sal | Sy | Dat |
|---|---|---|---|---|
| 119 | —OPh | — | 6 | F−: 346<br>N1: 3.01(3H, s), 4.21(3H, s), 4.43(2H, t), 5.13(2H, t), 6.8–7.0(3H, m), 7.2–7.4(2H, m), 7.9–8.1(2H, m), 8.1–8.3(2H, m) |
| 120 | —OBn | — | 6 | F−: 360<br>N1: 2.89(3H, s), 3.90(2H, t), 4.19(3H, s), 4.45(2H, s), 4.89(2H, t), 7.1–7.5(5H, m), 7.9–8.1(2H, m), 8.1–8.3(2H, m) |
| 121 | —NMe$_2$ | HCl | 6 | F: 298<br>N1: 2.8–3.0(6H, m), 3.02(3H, s), 3.5–3.8(2H, m), 4.16(3H, s), 5.0–5.2(2H, m), 7.9–8.1(2H, m), 8.1–8.3(2H, m), 11.2–11.5(1H, br) |
| 122 | —OEt | — | 6 | F: 299<br>N1: 1.06(3H, t), 2.89(3H, s), 3.44(2H, q), 3.80(2H, t), 4.20(3H, s), 4.86(2H, t), 7.9–8.1(2H, m), 8.1–8.3(2H, m) |
| 123 | —OPr | — | 6 | F: 313<br>N1: 0.80(3H, t), 1.3–1.6(2H, m), 2.90(3H, s), 3.35(2H, t), 3.80(2H, t), 4.20(3H, s), 4.87(2H, t), 7.9–8.1(2H, m), 8.1–8.3(2H, m) |
| 124 | —O(i-Pr) | — | 6 | F: 313<br>N1: 1.02(6H, d), 2.89(3H, s), 3.4–3.7(1H, m), 3.79(2H, t), 4.21(3H, s), 4.83(2H, t), 7.9–8.1(2H, m), 8.1–8.3(2H, m) |
| 125 | —O(CH$_2$)$_2$NH$_2$ | HCl | 6 | F: 314 |
| 126 | —OCH$_2$(Py3) | HCl | 6 | F: 362<br>N1: 2.90(3H, s), 3.98(2H, t), 4.21(3H, s), 4.68(2H, s), 4.95(2H, t), 7.8–8.1(3H, m), 8.1–8.4(3H, m), 8.6–8.9(2H, m) |
| 127 | —SMe | — | 6 | F: 301 |
| 128 | —SO$_2$Me | — | 6 | F: 333 |
| 129 | —NEt$_2$ | HCl | 6 | E: 326 |
| 130 | —N(i-Pr)$_2$ | HCl | 6 | E: 354 |
| 131 | -Pipe | HCl | 6 | E: 338 |
| 132 | -Morp | HCl | 6 | E: 340 |

TABLE 15

(Ib)

| Ex | —R$^1$ | Sal | Sy | Dat |
|---|---|---|---|---|
| 133 | —(CH$_2$)$_2$NHAc | — | 6 | F: 312<br>N1: 1.76(3H, s), 2.86(3H, s), 3.4–3.7(2H, m), 4.18(3H, s), 4.69(2H, t), 7.9–8.1(2H, m), 8.1–8.3(2H, m), 8.34(1H, t) |
| 134 | —(CH$_2$)$_2$OCONHPh | — | 6 | F: 390 |
| 135 | —(CH$_2$)$_3$OMe | — | 6 | F: 299<br>N1: 2.0–2.2(2H, m), 2.88(3H, s), 3.24(3H, s), 3.42(2H, t), 4.18(3H, s), 4.69(2H, t), 7.9–8.1(2H, m), 8.1–8.3(2H, m) |
| 136 | —(CH$_2$)$_3$NMe$_2$ | HCl | 6 | F: 312 |
| 137 | —CH$_2$(Py2) | HCl | 6 | F: 318<br>N1: 2.96(3H, s), 4.25(3H, s), 6.14(2H, s), 7.3–7.6(1H, m), 7.72(1H, d), 7.8–8.3(5H, m), 8.53(1H, d) |
| 138 | —CH$_2$(Py3) | HCl | 6 | F: 318 |
| 139 | —CH$_2$(Py4) | HCl | 6 | F: 318 |
| 140 | —CH$_2$CF$_3$ | — | 6 | F: 309 |

TABLE 15-continued (Ib)

| Ex | —R¹ | Sal | Sy | Dat |
|---|---|---|---|---|
| 141 | —(CH₂)₂CONH₂ | — | 6 | F: 298 |
| 142 | —(CH₂)₂CN | — | 6 | F: 280 |
| 143 | —(CH₂)₂O(CH₂)₂OMe | — | 6 | F: 329 |
| 144 | —CH₂Thf | — | 6 | F: 311 |
| 145 | —CH₂CONH₂ | — | 6 | F: 284 |
| 146 | —CH₂CN | — | 6 | F: 266 |

TABLE 16

(Ic)

| Ex | —R¹ | —R² | X | Sal | Sy | Dat |
|---|---|---|---|---|---|---|
| 7 | —Bn | —i-Pr | Br | — | — | F: 345<br>N1: 1.67(6H, d), 2.95(3H, s), 5.44(1H, br), 6.01(2H, s), 7.3–7.5(5H, m), 7.9–8.3(4H, m) |
| 147 | —Bn | —(CH₂)₂OH | Cl | — | 6 | F-: 346<br>N1: 2.88(3H, s), 3.86(2H, t), 4.75(2H, t), 6.02 (2H, s), 7.3–7.5(5H, m), 7.9–8.3(4H, m) |
| 148 | —(CH₂)₂OMe | —(CH₂)₂OMe | Cl | — | 6 | F-: 328<br>N1: 2.89(3H, s), 3.24(6H, s), 3.78(4H, t), 4.87 (4H, t), 7.9–8.1(2H, m), 8.1–8.3(2H, m) |
| 149 | —CH₂(Py4) | —Bn | Cl | HCl | 6 | F: 3.94 |
| 150 | —CH₂(Py3) | —Bn | Cl | HCl | 6 | F: 3.94 |
| 151 | —(CH₂)₂Ph | —(CH₂)₂OMe | Cl | — | 6 | F: 375 |
| 152 | —CH₂Th | —(CH₂)₂OMe | Cl | — | 6 | F: 367 |
| 153 | —CH₂Fu | —(CH₂)₂OMe | Cl | — | 6 | F: 351 |
| 154 | —CH₂Pyr | —(CH₂)₂OMe | Cl | — | 6 | F: 363<br>N1: 2.8–3.2(6H, m), 3.84(2H, t), 4.92(2H, t), 6.19(2H, s), 7.8–8.0(2H, m), 8.0–8.2(2H, m), 8.52(1H, dd), 8.62(1H, d), 8.92(1H, d) |
| 155 | —CH₂Qu | —(CH₂)₂OMe | Cl | HCl | 6 | F: 412 |
| 156 | —(CH₂)₂(Py2) | —(CH₂)₂OMe | Cl | HCl | 6 | F: 376 |
| 157 | —(CH₂)₂(Py3) | —(CH₂)₂OMe | Cl | HCl | 6 | F: 376 |
| 158 | —(CH₂)₂(Py4) | —(CH₂)₂OMe | Cl | HCl | 6 | F: 376 |
| 159 | —(CH₂)₂In | —(CH₂)₂OMe | Cl | — | 6 | F: 414 |
| 160 | —CH₂Dio | —(CH₂)₂OMe | Cl | — | 6 | F: 405 |
| 161 | —(CH₂)₃Im | —(CH₂)₂OMe | Cl | HCl | 6 | F: 379<br>N1: 2.3–2.6(2H, m), 2.98(3H, s), 3.27(3H, s), 3.79(2H, t), 4.45(2H, t), 4.76(2H, t), 4.86 (2H, t), 7.73(1H, d), 7.95(1H, d), 7.9–8.1 (2H, m), 8.1–8.3(2H, m), 9.40(1H, s), 15.14 (1H, br) |
| 162 | —(CH₂)₂Im | —(CH₂)₂OMe | Cl | HCl | 6 | F: 365<br>N1: 2.71(3H, s), 3.26(3H, s), 3.34(2H, t), 3.79 (2H, t), 4.81(2H, t), 5.00(2H, t), 7.50(1H, s), 7.9–8.1(2H, m), 8.1–8.3(2H, m), 9.04 (1H, s), 14.76(1H, br), 15.49(1H, br) |
| 163 | —CH₂Bim | —(CH₂)₂OMe | Cl | HCl | 6 | F: 401 |

TABLE 17

(Ic)

| Ex | —R¹ | —R² | X | Sal | Sy | Dat |
|---|---|---|---|---|---|---|
| 12 | —(CH₂)₂CO₂H | —Me | Cl | — | — | F+: 299 |
| 164 | —(CH₂)₂O(CH₂)₂—NH₂ | —(CH₂)₂OMe | Cl | HCl | 6 | F: 358 |
| 165 | —(CH₂)₅NH₂ | —(CH₂)₂OMe | Cl | HCl | 6 | F: 356 |
| 166 | —(CH₂)₂O(CH₂)₂—O(CH₂)₂NH₂ | —(CH₂)₂OMe | Cl | HCl | 6 | F: 402 |
| 167 | —CH(Me)Ph | —(CH₂)₂OMe | Cl | — | 6 | F: 375 |
| 168 | —CH₂(5-MePyr) | —(CH₂)₂OMe | Cl | — | 6 | F: 377 |
|  |  |  |  |  |  | N1: 2.99(3H, s), 3.27(3H, s), 3.82(2H, t), 4.92(2H, t), 6.13(2H, s), 7.9–8.1 (2H, m), 8.1–8.3(2H, m), 8.4–8.5(1H, m), 8.7–8.9(1H, m) |
| 169 | —CH₂Pyr | —CH₂Pyr | Cl | — | 6 | F: 397 |
|  |  |  |  |  |  | N1: 3.09(3H, br), 6.24(4H, br), 7.7–8.3(4H, m), 8.5–8.8(4H, m), 9.00(2H, d) |
| 170 | —CH₂(Py4) | —CH₂Pyr | Cl | — | 6 | F: 396 |
|  |  |  |  |  |  | N1: 2.96(3H, s), 6.11(2H, s), 6.20(2H, s), 7.3–7.5(2H, m), 7.8–8.1(2H, m), 8.0–8.2(2H, m), 8.5–8.8(4H, m), 9.01(1H, d) |
| 171 | [4-methylpiperidin-1-yl-NBn] | —Me | Cl | HCl | 6 | F: 400 |
| 172 | [4-methylpiperidin-1-yl-NCO₂Et] | —Me | Cl | — | 6 | F: 382 |
| 173 | [2-methoxy-methylcyclohexyl] | —Me | Cl | — | 6 | F: 339 |
| 174 | —(CH₂)₁₇Me | —(CH₂)₂OMe | Cl | — | 6 | F: 523 |
| 175 | —CH₂Ad | —(CH₂)₂OMe | Cl | — | 6 | F: 421 |
| 176 | —CH₂CHPh₂ | —(CH₂)₂OMe | Cl | — | 6 | F: 451 |
| 177 | —(CH₂)₂O(CH₂)₂—OMe | —(CH₂)₂OMe | Cl | — | 6 | F: 373 |
|  |  |  |  |  |  | N1: 2.91(3H, s), 3.15(3H, s), 3.24(3H, s), 3.3–3.4(2H, m), 3.4–3.6(2H, m), 3.79 (2H, t), 3.87(2H, t), 4.7–5.0(4H, m), 7.9–8.1(2H, m), 8.1–8.3(2H, m) |
| 178 | —(CH₂)₂O(CH₂)₂—O(CH₂)₂OMe | —(CH₂)₂OMe | Cl | — | 6 | F: 417 |
| 179 | —(CH₂)₂O(4-BnO—Ph) | —(CH₂)₂OMe | Cl | — | 6 | F: 497 |

TABLE 18

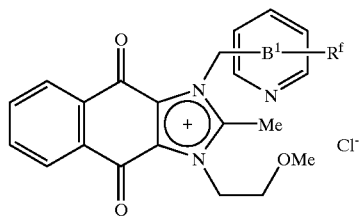

(Id)

| Ex | B¹ | —Rᶠ | Sal | Sy | Dat |
|---|---|---|---|---|---|
| 8 | Py3 | 2-OH | — | — | F: 378 |
| 9 | Py3 | 6-Cl | — | — | F: 396 |
|  |  |  |  |  | N1: 2.91(3H, s), 3.25(3H, s), 3.79(2H, t), 4.86(2H, t), 6.05 (2H, s), 7.59(1H, d), 7.87(1H, dd), 7.9–8.1(2H, m), 8.1–8.3 (2H, m), 8.45(1H, d) |
| 180 | Py3 | H | HCl | 6 | F: 362 |
|  |  |  |  |  | N1: 2.93(3H, s), 3.26(3H, s), 3.80(2H, t), 4.88(2H, t), 6.16 (2H, s), 7.8–8.3(6H, m), 8.7–8.9(2H, m) |
| 181 | Py2 | H | HCl | 6 | F: 362 |
|  |  |  |  |  | N1: 2.98(3H, s), 3.28(3H, s), 3.84(2H, t), 4.93(2H, t), 6.17 (2H, s), 7.3–7.6(1H, m), 7.71(1H, d), 7.8–8.4(5H, m), 8.52 (1H, d) |
| 182 | Py4 | H | HCl | 6 | F: 362 |
|  |  |  |  |  | N1: 2.92(3H, s), 3.28(3H, s), 3.83(2H, t), 4.92(2H, t), 6.35 (2H, s), 7.9–8.3(6H, m), 8.98(2H, d) |
| 183 | Py3 | 1-oxide | HCl | 6 | F: 378 |
| 184 | Py3 | 2-Cl | HCl | 6 | F: 396 |
|  |  |  |  |  | N1: 2.92(3H, s), 3.28(3H, s), 3.84(2H, t), 4.93(2H, t), 6.03 (2H, s), 7.3–7.6(2H, m), 7.9–8.0(2H, m), 8.0–8.3(2H, m), 8.42(1H, dd) |
| 185 | Py4 | 2-OH | — | 8 | F: 378 |
|  |  |  |  |  | N1: 2.84(3H, s), 3.26(3H, s), 3.81(2H, t), 4.88(2H, t), 5.84 (2H, s), 5.96(1H, s), 6.22(1H, dd), 7.44(1H, d), 7.9–8.1 (2H, m), 8.1–8.3(2H, m) |
| 186 | Py3 | 6-OMe | HCl | 6 | F: 392 |
|  |  |  |  |  | N1: 2.92(3H, s), 3.24(3H, s), 3.7–4.0(5H, m), 4.6–5.5(2H, m), 5.97(2H, s), 6.87(1H, d), 7.75(1H, d), 7.9–8.1(2H, m), 8.1–8.4(3H, m) |
| 187 | Py3 | 2-NMe₂ | HCl | 6 | F: 405 |
| 188 | Py3 | 6-NMe₂ | HCl | 6 | F: 405 |
| 189 | Py3 | 5-Me | HCl | 6 | F: 376 |
| 190 | Py3 | 6-Me | HCl | 6 | F: 376 |
| 191 | Py3 | 6-CF₃ | HCl | 6 | F: 430 |
| 192 | Py4 | 2-Cl | HCl | 6 | F: 396 |
|  |  |  |  |  | N1: 2.87(3H, s), 3.27(3H, s), 3.81(2H, t), 4.90(2H, t), 6.09 (2H, s), 7.3–7.5(3H, m), 7.8–8.4(4H, m), 8.45(1H, d) |
| 193 | Py4 | 2-NMe₂ | HCl | 6 | F: 405 |

TABLE 19

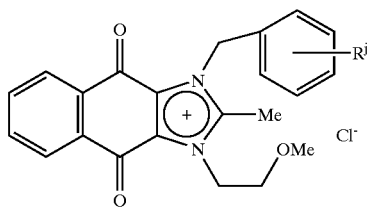

(Ie)

| Ex | —Rʲ | Sal | Sy | Dat |
|---|---|---|---|---|
| 194 | H | — | 6 | F: 361 |
|  |  |  |  | N1: 2.85(3H, s), 3.24(3H, s), 3.80(2H, t), 4.88(2H, t), 6.05 (3H, s), 7.2–7.5(5H, m), 7.9–8.3(4H, m) |
| 195 | 2-Cl | — | 6 | F: 395 |
| 196 | 3-Cl | — | 6 | F: 395 |

TABLE 19-continued
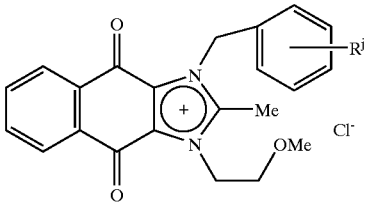
(Ie)
| Ex | —Rʲ | Sal | Sy | Dat |
|---|---|---|---|---|
| 197 | 4-Cl | — | 6 | F: 395<br>N1: 2.85(3H, s), 3.24(3H, s), 3.79(2H, t), 4.86(2H, t), 6.02 (2H, s), 7.34(2H, d), 7.48(2H, d), 7.9–8.1(2H, m), 8.1–8.3(2H, m) |
| 198 | 3,4-Cl | — | 6 | F+: 431 |
| 199 | 2-OMe | — | 6 | F: 391 |
| 200 | 3-OMe | — | 6 | F: 391 |
| 201 | 4-OMe | — | 6 | F: 391 |
| 202 | 4-Ph | — | 6 | F: 437 |
| 203 | 3-CN | — | 6 | F: 386 |
| 204 | 4-CN | — | 6 | F: 386 |
| 205 | 4-SO$_2$NH$_2$ | — | 6 | F: 440 |
| 206 | 4-CF$_3$ | — | 6 | F: 429 |
| 207 | 4-F | — | 6 | F: 379<br>N1: 2.87(3H, s), 3.24(3H, s), 3.79(2H, t), 4.87(2H, t), 6.03 (2H, s), 7.1–7.6(4H, m), 7.9–8.1(2H, m), 8.1–8.3(2H, m) |
| 208 | 4-Br | — | 6 | F: 439, 441 |
| 209 | 3-CH$_2$NH$_2$ | HCl | 6 | F: 390 |
| 210 | 4-CH$_2$NH$_2$ | HCl | 6 | F: 390 |
| 211 | 3-NO$_2$ | — | 6 | F: 406 |
| 212 | 4-NO$_2$ | — | 6 | F: 406<br>N1: 2.87(3H, s), 3.26(3H, s), 3.81(2H, t), 4.89(2H, t), 6.18 (2H, s), 7.61(2H, d), 7.9–8.4(6H, m) |
TABLE 20
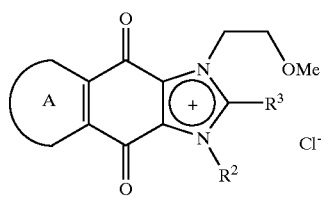
(If)
| Ex | A | —R² | —R³ | Sal | Sy | Dat |
|---|---|---|---|---|---|---|
| 213 | 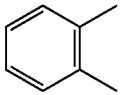 | —Me | —CH$_2$OMe | — | 6 | F: 315 |
| 214 | 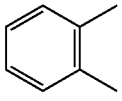 | —Me | —CH$_2$NMe$_2$ | HCl | 6 | F: 328 |
| 215 | 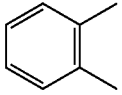 | —(CH$_2$)$_4$— | | — | 6 | F: 311 |

TABLE 20-continued (If)

| Ex | A | —R² | —R³ | Sal | Sy | Dat |
|---|---|---|---|---|---|---|
| 216 | 2,3-dimethyl-nitrobenzene | —(CH₂)₂OMe | —Me | — | 6 | F: 374<br>N1: 2.90(3H, s), 3.72(2H, t), 3.77 (2H, t), 4.81(2H, t), 4.87(2H, t), 8.1–8.5(3H, m) |
| 217 | 2,3-dimethyl-pyridine | —(CH₂)₂OMe | —Me | HCl | 6 | F: 330 |
| 218 | MeO₂C-methylthiophene | —(CH₂)₂OMe | —Me | — | 6 | F: 393 |

TABLE 21

(Ig)

| Co | R¹ | R² | R³ |
|---|---|---|---|
| 1 | —CH₂CH=CH—CH₂OMe | —(CH₂)₂N(Bn)₂ | Me |
| 2 | —(CH₂)₂OMe | —CH(Ph)CO₂Et | Me |
| 3 | —(CH₂)₂OMe | —(CH₂)₂SO₂NH₂ | Me |
| 4 | Me | —(CH₂)₂SCH₂Ph | Me |
| 5 | —(CH₂)₂OMe | —(CH₂)₂CO₂H | Me |
| 6 | —(CH₂)₂OMe | —(CH₂)₂CO(Pyr) | Me |
| 7 | —(CH₂)₂OMe | —(CH₂)₂CONH₂ | Me |
| 8 | —(CH₂)₂OMe | —(CH₂)₂—N[(CH₂)₂NMe₂]₂ | Me |
| 9 | —(CH₂)₂OMe | —(CH₂)₂O(CH₂)₂—NH(CH₂)₂NMe₂ | Me |
| 10 | —(CH₂)₂OMe | —(CH₂)₂O(Py4) | Me |
| 11 | —CH₂C≡C—CH₂OMe | —(CH₂)₂—NHCONH₂ | Me |
| 12 | —(CH₂)₂OMe | —(CH₂)₂CO₂Me | Me |
| 13 | —(CH₂)₂OMe | Me | CF₃ |
| 14 | —CH₂(Pyr) | —(CH₂)₂OMe | H |
| 15 | —(CH₂)₂OMe | —(CH₂)₂O—(CH₂)₂NMe₂ | Me |
| 16 | —(CH₂)₂O—(c-Pr) | —(CH₂)₂OMe | Me |
| 17 | —(CH₂)₂OMe | —(CH₂)₂OCH₂— | |
| 18 | —(CH₂)₂OMe | —(CH₂)₂N(Me)—COPh | Me |
| 19 | Me | —(CH₂)₂NO₂ | Me |
| 20 | —(CH₂)₂OMe | —(CH₂)₂CN | Me |
| 21 | —(CH₂)₂OMe | —CH₂COPh | Me |
| 22 | —(CH₂)₂OMe | —CH₂CONH₂ | Me |
| 23 | —(CH₂)₂OMe | —(CH₂)₂OAc | Me |
| 24 | Me | —(CH₂)₂Ac— | Me |
| 25 | —(CH₂)₂NH—(CH₂)₂NH₂ | —(CH₂)₂—N(Me)Bn | Me |
| 26 | —(CH₂)₂OMe | —(CH₂)₂—NHSO₂Me | Me |
| 27 | —(CH₂)₂OMe | —(CH₂)₂—CONHOMe | Me |
| 28 | —(CH₂)₂OMe | —(CH₂)₂OCO—CH₂CO₂Et | Me |
| 29 | Me | —(CH₂)₂SOMe | Me |
| 30 | —(CH₂)₂OMe | Me | c-Pr |
| 31 | Me | —(CH₂)₂OMe | —(CH₂)₂OMe |
| 32 | —(CH₂)₂OMe | —(CH₂)₃O—(CH₂)₂NMe₂ | Me |
| 33 | —(CH₂)₂O—(CH₂)₂(Morp) | —(CH₂)₂OMe | Me |
| 34 | —(CH₂)₂OMe | —(CH₂)₂N(Me)CH₂— | |

TABLE 22

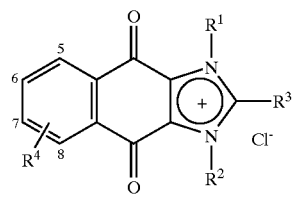

(Ih)

| Co | R¹ | R³ | R⁴ |
|---|---|---|---|
| 35 | —CH₂(Py4) | Me | 7-CF₃ |
| 36 | —CH₂(Py3) | Me | 5-CH₂NH₂ |
| 37 | —CH₂(Pyr) | H | 6-NMe₂ |
| 38 | —(CH₂)₂OMe | Me | 5-NO₂ |

TABLE 23

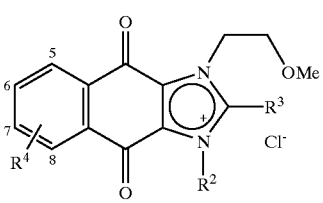

(Ii)

| Co | R² | R³ | R⁴ |
|---|---|---|---|
| 39 | —CH₂(Pyr) | Me | 5-F |
| 40 | —CH₂(Py4) | Me | 6-F |
| 41 | —(CH₂)₂OMe | Me | 7-F |
| 42 | —CH₂(Py3) | H | 8-F |
| 43 | —CH₂(Pyr) | Me | 8-CN |
| 44 | —CH₂(Py3) | Me | 5-CF₃ |
| 45 | —(CH₂)₂OMe | Et | 6-CF₃ |
| 46 | —(CH₂)₂OMe | Me | 5,8-OH |
| 47 | —CH₂(Py4) | Me | 8-CH₂NH₂ |
| 48 | —CH₂(Py4) | Me | 7-Me |
| 49 | —CH₂(Py3) | Me | 8-Me |
| 50 | —(CH₂)₂OMe | Me | 7-NMe₂ |
| 51 | —CH₂(Py4) | Me | 8-NMe₂ |
| 52 | —CH₂(Pyr) | Me | 6,7-diMe |
| 53 | —CH₂(Py4) | H | 6-NO₂ |
| 54 | —(CH₂)₂OMe | Me | 5-Me |
| 55 | —CH₂(Pyr) | i-Pr | 6-Me |
| 56 | —(CH₂)₂OMe | Me | 5-CH₂NMe₂ |
| 57 | —CH₂(Py4) | i-Pr | 5-OMe |
| 58 | —CH₂(Py3) | Me | 6-OMe |
| 59 | —CH₂(Pyr) | Me | 7-OMe |
| 60 | —(CH₂)₂OMe | Me | 8-OMe |
| 61 | —CH₂(Py4) | Me | 5-CN |
| 62 | —CH₂(Py3) | Et | 6-CN |
| 63 | —(CH₂)₂OMe | Me | 7-CN |
| 64 | —CH₂(Pyr) | Me | 8-CF₃ |
| 65 | —(CH₂)₂OMe | Me | 5-CH₂N(Me)Bn |
| 66 | —(CH₂)₂OMe | H | 6-CH₂NH₂ |
| 67 | —CH₂(Pyr) | Me | 7-CH₂NH₂ |

TABLE 23-continued

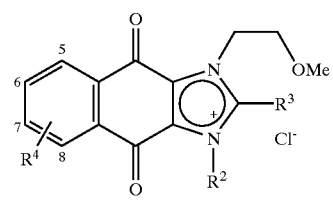

(Ii)

| Co | R² | R³ | R⁴ |
|---|---|---|---|
| 68 | —CH₂(Py4) | Me | 6-Me,7-F |
| 69 | —CH₂(Py3) | Me | 5-NMe₂ |
| 70 | —(CH₂)₂OMe | Me | 5,8-OMe |
| 71 | —(CH₂)₂OMe | Me | 5-CH₂N(Me)COPh |
| 72 | —CH₂(Py3) | Me | 7-NO₂ |
| 73 | —CH₂(Pyr) | Me | 8-NO₂ |
| 74 | —(CH₂)₂OMe | Me | 5-CH₂(Morp) |

TABLE 24

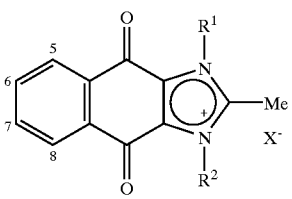

(Ij)

| Co | R¹ | R² | X |
|---|---|---|---|
| 75 | —CH₂(Pyr) | —(CH₂)₂OMe | Br |
| 76 | —CH₂(Py3) | —(CH₂)₂OMe | Br |
| 77 | —CH₂(Py4) | —(CH₂)₂OMe | AcO |
| 78 | —CH₂(Pyr) | —(CH₂)₂OMe | AcO |
| 79 | —CH₂(Py3) | —(CH₂)₂OMe | PhSO₃ |
| 80 | —(CH₂)₂OMe | —(CH₂)₂OMe | PhSO₃ |
| 81 | —CH₂(Pyr) | —(CH₂)₂CO₂⁻ | — |
| 82 | —CH₂(Py4) | —(CH₂)₂CO₂⁻ | — |
| 83 | —CH₂(Py3) | —CH₂CO₂⁻ | — |
| 84 | —(CH₂)₂OMe | —CH₂CO₂⁻ | — |
| 85 | —CH₂(Py4) | —(CH₂)₂OMe | I |
| 86 | —(CH₂)₂OMe | —(CH₂)₂OMe | I |

TABLE 25

(Ik) — structure: naphthoquinone fused imidazolium with R¹ on N, Me on C2, R² on N; Cl⁻ counterion; positions 5,6,7,8 on benzo ring.

| Co | R¹ | R² |
|---|---|---|
| 87 | —(CH$_2$)$_2$OMe | —CH$_2$CO—(2-CO$_2$Et-phenoxy) |
| 88 | —(CH$_2$)$_2$—(5-Me-pyrazin-2-yl) | —(CH$_2$)$_2$OMe |
| 89 | —(CH$_2$)$_2$OMe | —(CH$_2$)$_2$—(5-CN-pyrazin-2-yl) |
| 90 | —(CH$_2$)$_2$OMe | —CH$_2$—(5-Cl-pyrazin-2-yl) |
| 91 | —(CH$_2$)$_2$OMe | —(CH$_2$)$_2$—(4-NMe$_2$-piperidin-1-yl) |
| 92 | —(CH$_2$)$_2$OMe | —CH$_2$—(pyridazin-4-yl) |
| 93 | —(CH$_2$)$_2$OMe | —CH$_2$—(4-(2-methoxyethoxy)phenyl) |
| 94 | —CH$_2$—(2-Me-thiazol-4-yl) | —(CH$_2$)$_2$OMe |
| 95 | —(CH$_2$)$_2$OMe | —CH$_2$—(oxazol-5-yl) |
| 96 | —(CH$_2$)$_2$OMe | —(CH$_2$)$_2$—(5-Me-pyrazin-2-yl) |
| 97 | —(CH$_2$)$_2$OMe | —(CH$_2$)$_2$—(4-NMe$_2$-cyclohex-1-en-1-yl) |

TABLE 25-continued
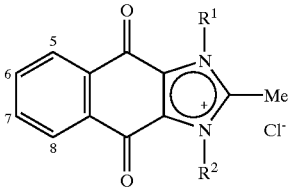
(Ik)
| Co | R¹ | R² |
|---|---|---|
| 98 | Me | 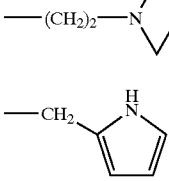 |
| 99 | —(CH₂)₂OMe |  |
| 100 | 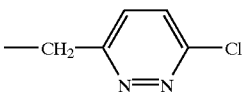 | —(CH₂)₂OMe |
| 101 | —(CH₂)₂OMe | 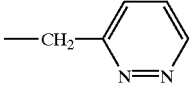 |
| 102 | —(CH₂)₂OMe | 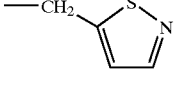 |
| 103 | Me | 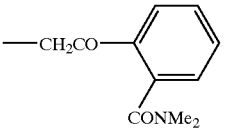 |
| 104 | 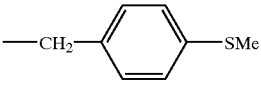 | —(CH₂)₂OMe |
| 105 | 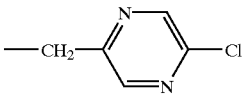 | —(CH₂)₂OMe |
| 106 | —(CH₂)₂OMe | 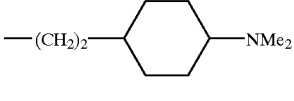 |
| 107 | Me | 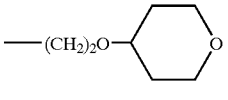 |
| 108 | —(CH₂)₂OMe | —(CH₂)₂O— (tetrahydropyran-4-yl) |
| 109 | —(CH₂)₂OMe | 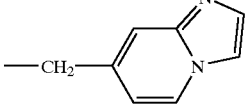 |

TABLE 25-continued (Ik)

| Co | R¹ | R² |
|---|---|---|
| 110 | —(CH₂)₂OMe | —CH₂-(pyrimidin-5-yl) |
| 111 | —CH₂-(5-Ac-pyrazin-2-yl) | Me |
| 112 | —(CH₂)₂OMe | —CH₂-C₆H₄-4-OAc |
| 113 | —(CH₂)₂OMe | —CH₂-C₆H₄-4-NHAc |
| 114 | —(CH₂)₂OMe | —CH₂-(pyrimidin-2-yl) |
| 115 | —(CH₂)₂OMe | —CH₂-(pyrimidin-4-yl) |
| 116 | —CH₂-(1,2,4-thiadiazol-5-yl) | —(CH₂)₂OMe |
| 117 | Me | —CH₂-(2H-tetrazol-5-yl) |
| 118 | —(CH₂)₂OMe | —CH₂-(5-Cl-pyrimidin-2-yl) |
| 119 | —CH₂-(2-Cl-pyrimidin-5-yl) | —(CH₂)₂OMe |
| 120 | —CH₂-(thiazol-2-yl) | —(CH₂)₂OMe |

TABLE 26

| Co | R¹ | R² |
|---|---|---|
| 121 | —CH₂-(1,2,4-oxadiazol-3-yl) | —(CH₂)₂OMe |
| 122 | —(CH₂)₂OMe | —CH₂-(isoxazol-5-yl) |
| 123 | —(CH₂)₂OMe | —CH₂O(CH₂)₂-phthalimidyl |
| 124 | —(CH₂)₂OMe | —CH₂OCH₂-(4-Cl-phenyl) |
| 125 | —(CH₂)₂OMe | —CH₂-(thiazol-4-yl) |
| 126 | —(CH₂)₂OMe | —CH₂-(imidazo[1,2-a]pyrimidin-7-yl) |
| 127 | —(CH₂)₂OMe | —CH₂-(1-Me-1,2,4-triazol-3-yl) |
| 128 | —(CH₂)₂OMe | —CH₂OCH₂-(1,3-dioxan-2-yl) |
| 129 | —(CH₂)₂OMe | —CH₂OCH₂-(2-MeO-phenyl) |
| 130 | —CH₂-(2-(pyridin-4-yl)thiazol-4-yl) | —(CH₂)₂OMe |

TABLE 27

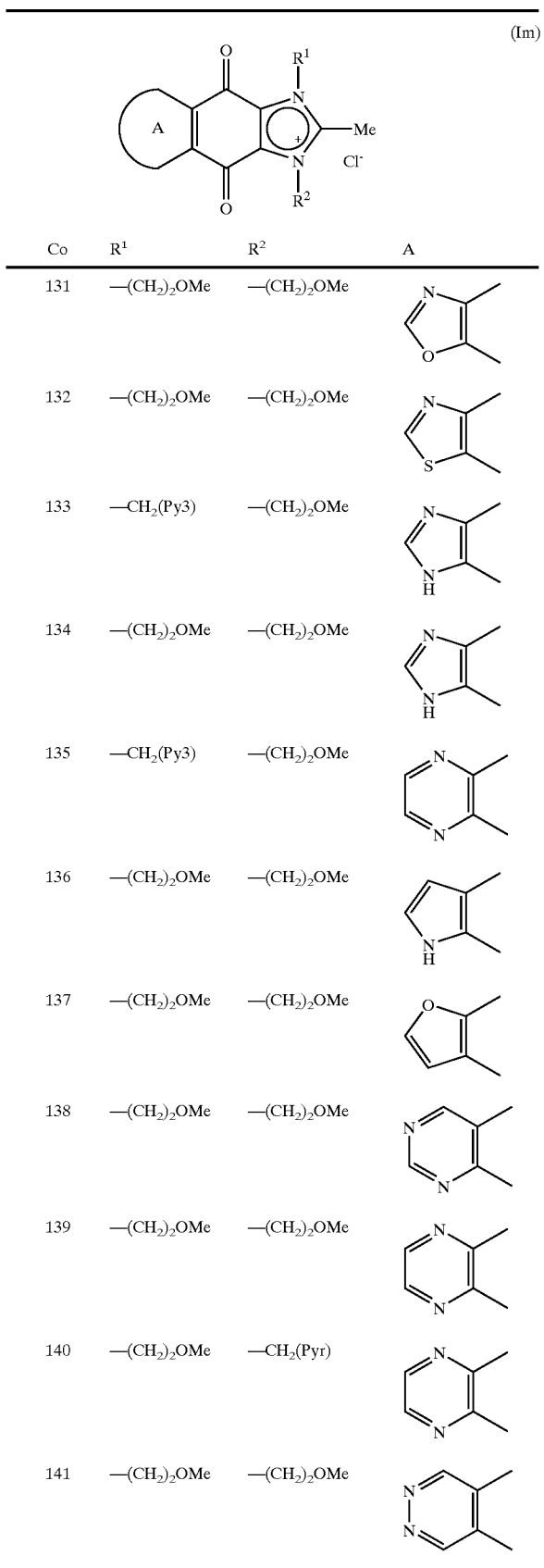

(Im)

| Co | R¹ | R² | A |
|---|---|---|---|
| 131 | —(CH₂)₂OMe | —(CH₂)₂OMe | oxazole |
| 132 | —(CH₂)₂OMe | —(CH₂)₂OMe | thiazole |
| 133 | —CH₂(Py3) | —(CH₂)₂OMe | imidazole |
| 134 | —(CH₂)₂OMe | —(CH₂)₂OMe | imidazole |
| 135 | —CH₂(Py3) | —(CH₂)₂OMe | dimethylpyrazine |
| 136 | —(CH₂)₂OMe | —(CH₂)₂OMe | pyrrole |
| 137 | —(CH₂)₂OMe | —(CH₂)₂OMe | furan |
| 138 | —(CH₂)₂OMe | —(CH₂)₂OMe | pyrimidine |
| 139 | —(CH₂)₂OMe | —(CH₂)₂OMe | pyrazine |
| 140 | —(CH₂)₂OMe | —CH₂(Pyr) | pyrazine |
| 141 | —(CH₂)₂OMe | —(CH₂)₂OMe | pyridazine |

TABLE 27-continued

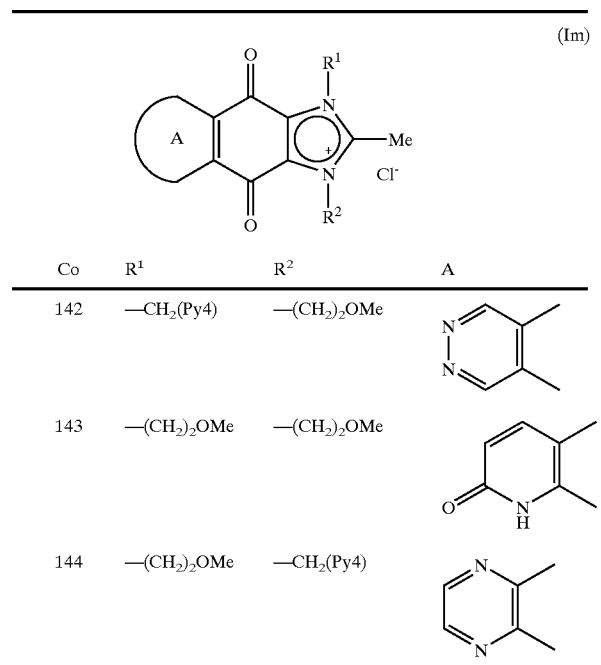

(Im)

| Co | R¹ | R² | A |
|---|---|---|---|
| 142 | —CH₂(Py4) | —(CH₂)₂OMe | dimethylpyridazine |
| 143 | —(CH₂)₂OMe | —(CH₂)₂OMe | pyridinone |
| 144 | —(CH₂)₂OMe | —CH₂(Py4) | dimethylpyrazine |

What is claimed is:

1. A fused imidazolium derivative represented by the following general formula (I)

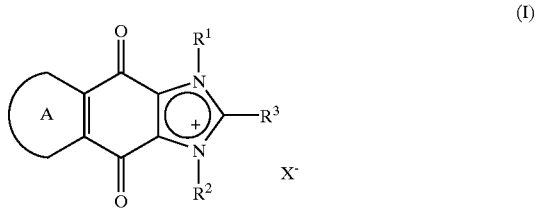

(I)

(wherein symbols in the formula have the following meanings;

R¹ and R²: the same or different from each other and each represents -(lower alkyl having one or more substituents selected from group B), -(lower alkenyl having one or more substituents selected from group B), -(lower alkynyl having one or more substituents selected from group B), -RinD, -lower alkyl, -lower alkenyl or -lower alkynyl, with the proviso that at least one of R¹ and R² is -(lower alkyl having one or more substituents selected from group B), -(lower alkenyl having one or more substituents selected from group B), -(lower alkynyl having one or more substituents selected from group B), -(cycloalkyl having one or more substituents) or -(five- to seven-membered saturated heterocyclic ring which may have one or more substituents), group B: —OR$^a$, —SR$^a$, -prodrug-formed OH, —O-lower alkylene-OR$^a$, —O-lower alkylene-O-lower alkylene-OR$^a$, —O-lower alkylene-NR$^a$R$^b$, —O-lower alkylene-O-lower alkylene-NR$^a$R$^b$, —O-lower alkylene-NR$^c$-lower alkylene-NR$^a$R$^b$, —OCO—NR$^a$R$^b$, —SOR$^a$, —SO₂R$^a$, —SO₂NR$^a$R$^b$, —NR$^a$—SO₂R$^b$, —NR$^a$R$^b$, —NR$^c$-lower alkylene-NR$^a$R$^b$, —N(-lower alkylene-NR$^a$R$^b$)₂, -RinD, —NO₂, —CN, -halogen, —CO$_2$R$^a$, —COO$^-$, —CONR$^a$R$^b$, —CONR$^a$—O—R$^b$, —NR$^a$—COR$^b$, —NR$^a$—CO—NR$^b$R$^c$, —OCOR$^a$ and —CO—R$^a$, R$^a$, R$^b$ and R$^c$: the same or different from one another and each represents —H, -lower alkyl, -lower alkylene-RinD or -RinD, RinD: -(five- to seven-membered saturated heterocyclic ring which may have one or more substituents), -(cycloalkyl which may have one or more substituents), -(cycloalkenyl which may have one or more substituents), -(aryl which may have one or more substituents) or -(heteroaryl which may have one or more substituents), R$^3$: —H or -(lower alkyl which may have one or more substituents), or R$^2$ and R$^3$ may together form a lower alkylene having from 2 to 5 carbon atoms which may be interrupted with O, S or NR$^4$ (R$^4$: —H or -lower alkyl), ring A: aryl ring which may have one or more substituents or heteroaryl ring which may have one or more substituents, and X$^-$: counter anion, with the proviso that X$^-$ does not exist when the substituent —COO$^-$ of the group B forms intramolecular salt with imidazolium cation, with the proviso that compounds having the following combinations of R$^1$ and R$^2$ are excluded:

(1) one is -lower alkylene-(aryl which may have one or more substituents) and the other is —CH$_3$, —(CH$_2$)$_3$CH$_3$ or -phenyl, (2) one is -lower alkylene-CO-(aryl which may have one or more substituents) and the other is —CH$_2$CH(CH$_3$)$_2$ or —(CH$_2$)$_3$CH$_3$, or (3) R$^1$ and R$^2$ are both -benzyl, —(CH$_2$)$_2$OC$_2$H$_5$ or —(CH$_2$)$_2$O—COCH$_3$.

2. The fused imidazolium derivative according to claim 1, wherein at least one of R$^1$ and R$^2$ is -(lower alkyl having one or more substituents selected from group B), -(lower alkenyl having one or more substituents selected from group B), -(lower alkynyl having one or more substituents selected from group B), -(cycloalkyl having one or more substituents selected from group C) or -(five- to seven-membered saturated heterocyclic ring which may have one or more substituents selected from group C); group C is -lower alkyl, -halogen, -halogeno lower alkyl, —OR$^a$, —O-lower alkylene-OR$^a$, —SR$^a$, —NR$^a$R$^b$, —NO$_2$, —CN, —CO$_2$R$^a$, —CO—NR$^a$R$^b$, —COR$^a$, —NR$^a$—COR$^b$, —SO$_2$NR$^a$R$^b$, -lower alkylene-NR$^a$R$^b$, -aryl, -lower alkylene-aryl and —OCO—R$^a$; RinD is -(five- to seven-membered saturated heterocyclic ring which may have one or more substituents selected from group C), -(cycloalkyl which may have one or more substituents selected from group C), -(cycloalkenyl which may have one or more substituents selected from group C), -(aryl which may have one or more substituents selected from group C) or -(heteroaryl which may have one or more substituents selected from group C); R$^3$ is —H or -(lower alkyl which may have one or more substituents selected from group B), or R$^2$ and R$^3$ may together form a lower alkylene having from 2 to 5 carbon atoms which may be interrupted with O, S or NR$^4$; and ring A is aryl ring which may have one or more substituents selected from group C or heteroaryl ring which may have one or more substituents selected from group C.

3. The fused imidazolium derivative according to claim 2, wherein at least one of R$^1$ and R$^2$ is a lower alkyl having one or more substituents selected from group B; R$^3$ is methyl group; and ring A is benzene ring which may have one or more substituents selected from group C or heteroaryl ring selected from thiophene, furan, pyrrole, imidazole, oxazole, thiazole, pyridine, pyrazine, pyridazine and pyrimidine rings, which may have one or more substituents selected from group C.

4. The fused imidazolium derivative according to claim 2 or 3, wherein at least one of R$^1$ and R$^2$ is a lower alkyl having one or more substituents selected from the group consisting of —OR$^a$, —NR$^a$R$^b$, —NR$^a$—COR$^b$, —O-lower alkylene-OR$^a$, —O-lower alkylene-O-lower alkylene-OR$^a$, —SR$^a$, —CONR$^a$R$^b$, —CN, -(cycloalkyl which may have one or more substituents selected from group C), -(five- to seven-membered saturated heterocyclic ring which may have one or more substituents selected from group C), -(aryl which may have one or more substituents selected from group C) and -(heteroaryl which may have one or more substituents selected from group C).

5. The fused imidazolium derivative according to claim 2 or 3, wherein at least one of R$^1$ and R$^2$ is a lower alkyl having one substituent selected from the group consisting of -(heteroaryl selected from pyridyl, pyrazinyl and pyrimidinyl, which may have one or more substituents selected from group C), —O-lower alkylene-O-lower alkyl and —O-lower alkyl, and ring A is benzene ring which may be substituted by —NO$_2$.

6. The fused imidazolium derivative according to claim 1, wherein it is selected from 1-[(6-chloro-3-pyridyl)methyl]-3-(2-methoxyethyl)-2-methyl-4,9-dioxo-4,9-dihydro-1H-naphtho[2,3-d]imidazol-3ium, 1,2-dimethyl-4,9-dioxo-3-[(2-tetrahydrofuranyl)methyl]-4,9-dihydro-1H-naphtho[2,3-d]imidazol-3-ium, 1,3-bis(2-methoxyethyl)-2-methyl-4,9-dioxo-4,9-dihydro-1H-naphtho[2,3-d]imidazol-3-ium, 3-(2-methoxyethyl)-2-methyl-4,9-dioxo-4,9-dihydro-1-(2-pyrazinylmethyl)-4,9-dihydro-1H-naphtho[2,3-d]imidazol-3-ium, 1-[3-(1H-4-imidazolyl)propyl]-3-(2-methoxyethyl)-2-methyl-4,9-dioxo-4,9-dihydro-1H-naphtho[2,3-d] imidazol-3-ium, 3-(2-methoxyethyl)-2-methyl-1-[(5-methyl-2-pyrazinyl)methyl]-4,9-dioxo-4,9-dihydro-1H-naphtho[2,3-d]imidazol-3-ium, 2-methyl-4,9-dioxo-1,3-bis(2-pyrazinylmethyl)-4,9-dihydro-1H-naphtho[2,3-d] imidazol-3ium, 1-[2-(2-methoxyethoxy)ethyl[-3-(2-methoxyethyl)-2-methyl-4,9-dioxo-4,9-dihydro-1H-naphtho[2,3-d]imidazol-3-ium, 1-{2-[2-(2-methoxyethoxy) ethoxy]ethyl}-3-(2-methoxyethyl)-2-methyl-4,9-dioxo-4,9-dihydro-1H-naphtho[2,3-d]imidazol-3-ium, 1-(2-methoxyethyl)-2-methyl-4,9-dioxo-3-(3-pyridylmethyl)-4, 9-dihydro-1H-naphtho[2,3-d]imidazol-3-ium, 3-(2-methoxyethyl)-2-methyl-4,9-dioxo-1-(2-pyridylmethyl)-4, 9-dihydro-1H-naphtho[2,3-d]imidazol-3-ium, 3-(2-methoxyethyl)-2-methyl-4,9-dioxo-1-(4-pyridylmethyl)-4, 9-dihydro-1H-naphtho]2,3-d]imidazol-3-ium, 1-[(2-chloro-3-pyridyl)methyl]-3-(2-methoxyethyl)-2-methyl-4,9-dioxo-4,9-dihydro-1H-naphtho[2,3-d]imidazol-3-ium, 1-[(2-hydroxy-4-pyridyl)methyl]-3-(2-methoxyethyl)-2-methyl-4,9-dioxo-4,9-dihydro-1H-naphtho[2,3-d]imidazol-3-ium, 3-(2-methoxyethyl)-1-[(6-methoxy-3-pyridyl)methyl]-2-methyl-4,9-dioxo-4,9-dihydro-1H-naphtho[2,3-d]imidazol-3-ium, 1-[(2-chloro-4-pyridyl)methyl]-3-(2-methoxyethyl)-2-methyl-4,9-dioxo-4,9-dihydro-1H-naphtho[2,3-d] imidazol-3-ium, 1-(4-chlorobenzyl)-3-(2-methoxyethyl)-2-methyl-4,9-dioxo-4,9-dihydro-1H-naphtho[2,3-d]imidazol- 3-ium, 1-(4-fluorobenzyl)-3-(2-methoxyethyl)-2methyl-4,9-dioxo-4,9-dihydro-1H-naphtho[2,3-d]imidazol-3-ium and 1,3-bis(2-methoxyethyl)-2-methyl-5-nitro-4,9-dioxo-4,9-dihydro-1H-naphtho[2,3-d]imidazol-3-ium or tautomers thereof and their salts with halogen ions.

7. A pharmaceutical composition which comprises the fused imidazolium derivative of claim 1 and a pharmaceutically acceptable carrier.

8. The pharmaceutical composition according to claim 7, wherein it is an anticancer agent.

9. A fused imidazole derivative represented by the following general formula (III) or a salt thereof

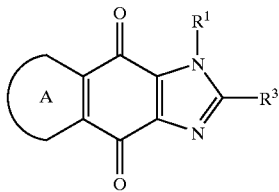

(III)

(wherein symbols in the formula have the following meanings;

$R^1$: a lower alkyl having one or more substituents selected from the group consisting of —ORa, —O-lower alkylene-ORa, -lower alkylene-O-lower alkylene-ORa, -(five- to seven-membered saturated heterocyclic ring which may have one or more substituents selected from the group C), -(aryl which may have one or more substiuents selected from the group C) and -(heteroaryl which may have one or more substituents selected from the group C), with the proviso that a lower alkyl group having one or more substituents selected from the group consisting of —OH, and -(phenyl which may be substituted by —Cl, —F, —Me or —OMe) is excluded, Group C: -lower alkyl, -halogen, -halogeno lower alkyl, —OH, —O-lower alkyl, —O-lower alkylene-OH, —O-lower alkylene-O-lower alkyl, -lower alkylene-$NH_2$, $NH_2$, —NH-lower alkyl, —N (lower alkyl)$_2$, —$CO_2H$, —$CO_2$-lower alkyl, —CO—$NH_2$, —$SO_2$—$NH_2$, —$NO_2$ and —CN, $R^a$, —H, -lower alkyl, -lower alkylene-RinD or -RinD, RinD: -(five- to seven-membered saturated heterocyclic ring which may have one or more substituents), -(cycloalkyl which may have one or more substituents), -(cycloalkenyl which may have one or more substituents), -(aryl which may have one or more substituents) or -(heteroaryl which may have one or more substituents), $R^3$: —H or -(lower alkyl which may have one or more substituents), and ring A: benzene ring which may be substituted by —$NO_2$).

* * * * *